US011801003B2

(12) United States Patent
Shapiro et al.

(10) Patent No.: US 11,801,003 B2
(45) Date of Patent: Oct. 31, 2023

(54) ESTIMATING THE MAGNETIC FIELD AT DISTANCES FROM DIRECT MEASUREMENTS TO ENABLE FINE SENSORS TO MEASURE THE MAGNETIC FIELD FROM THE BRAIN USING A NEURAL DETECTION SYSTEM

(71) Applicant: HI LLC, Los Angeles, CA (US)

(72) Inventors: Benjamin Shapiro, Culver City, CA (US); Ricardo Jimenez-Martinez, Culver City, CA (US); Julian Kates-Harbeck, Marina Del Rey, CA (US); Zachary Bednarke, Los Angeles, CA (US); Jamu Alford, Lake Arrowhead, CA (US)

(73) Assignee: HI LLC, Los Angeles, CA (US)

( * ) Notice: Subject to any disclaimer, the term of this patent is extended or adjusted under 35 U.S.C. 154(b) by 226 days.

(21) Appl. No.: 17/160,152

(22) Filed: Jan. 27, 2021

(65) Prior Publication Data

US 2021/0244330 A1 Aug. 12, 2021

Related U.S. Application Data

(60) Provisional application No. 63/035,664, filed on Jun. 5, 2020, provisional application No. 62/975,719, filed on Feb. 12, 2020.

(51) Int. Cl.
*A61B 5/245* (2021.01)
*A61B 5/00* (2006.01)

(52) U.S. Cl.
CPC ............ *A61B 5/245* (2021.01); *A61B 5/6803* (2013.01); *A61B 2562/0223* (2013.01); *A61B 2562/046* (2013.01)

(58) Field of Classification Search
CPC ...... A61B 2562/0223; A61B 2562/046; A61B 5/245; A61B 5/248; A61B 5/6803; A61B 5/7214
See application file for complete search history.

(56) References Cited

U.S. PATENT DOCUMENTS 3,173,082 A 3/1965 Bell et al.
3,257,608 A 6/1966 Bell et al.
(Continued)

FOREIGN PATENT DOCUMENTS

CN 104730484 6/2015
CN 107562188 1/2018
(Continued)

OTHER PUBLICATIONS

Adlene Hicheiur, "Parameterization of the LHCb magnetic field map" (Year: 2007).*

(Continued)

*Primary Examiner* — Katherine L Fernandez
*Assistant Examiner* — Brooke Lyn Klein
(74) *Attorney, Agent, or Firm* — Michael J. Bolan; Vista IP Law Group, LLP

(57) ABSTRACT

At least one magnetic field actuator is configured for generating an actuated magnetic field that at least partially cancels an outside magnetic field, thereby yielding a total residual magnetic field. A plurality of magnetometers are configured for taking measurements of the total residual magnetic field. The magnetometers include a plurality of coarse magnetometers and a plurality of fine magnetometers. A processor is configured for acquiring the total residual magnetic field measurements from the coarse magnetometers, estimating the total residual magnetic field at the fine magnetometers based on total residual magnetic field measurements acquired from the plurality of coarse magne- (Continued)

tometers, and controlling the actuated magnetic field at least partially based on the total residual magnetic field estimates at the fine magnetometers in a manner that suppresses the total residual magnetic field at the fine magnetometers to a baseline level, such that at least one of the fine magnetometers is in-range.

27 Claims, 9 Drawing Sheets

(56) References Cited

U.S. PATENT DOCUMENTS

| | | | |
|---|---|---|---|
| 3,495,161 A | 2/1970 | Bell | |
| 3,501,689 A | 3/1970 | Robbiano | |
| 3,513,381 A | 5/1970 | Happer, Jr. | |
| 4,193,029 A | 3/1980 | Cioccio et al. | |
| 4,951,674 A | 8/1990 | Zanakis et al. | |
| 5,189,368 A | 2/1993 | Chase | |
| 5,192,921 A | 3/1993 | Chantry et al. | |
| 5,225,778 A | 7/1993 | Challlout et al. | |
| 5,254,947 A | 10/1993 | Chaillout et al. | |
| 5,309,095 A | 5/1994 | Ahonen et al. | |
| 5,442,289 A | 8/1995 | Dilorio et al. | |
| 5,444,372 A | 8/1995 | Wikswo, Jr. et al. | |
| 5,471,985 A | 12/1995 | Warden | |
| 5,506,200 A | 4/1996 | Hirschkoff et al. | |
| 5,526,811 A | 6/1996 | Lypchuk | |
| 5,713,354 A | 2/1998 | Warden | |
| 6,144,872 A | 11/2000 | Graetz | |
| 6,242,907 B1 * | 6/2001 | Clymer | G01B 7/30 324/207.17 |
| 6,339,328 B1 | 1/2002 | Keena et al. | |
| 6,472,869 B1 | 10/2002 | Upschulte et al. | |
| 6,665,553 B2 | 12/2003 | Kandori et al. | |
| 6,806,784 B2 | 10/2004 | Hollberg et al. | |
| 6,831,522 B2 | 12/2004 | Kitching et al. | |
| 7,038,450 B2 | 5/2006 | Romalis et al. | |
| 7,102,451 B2 | 9/2006 | Happer et al. | |
| 7,145,333 B2 | 12/2006 | Romalis et al. | |
| 7,269,532 B2 * | 9/2007 | David | G01C 21/185 702/141 |
| 7,521,928 B2 | 4/2009 | Romalis et al. | |
| 7,656,154 B2 | 2/2010 | Kawabata et al. | |
| 7,826,065 B1 | 11/2010 | Okanden et al. | |
| 7,872,473 B2 | 1/2011 | Kitching et al. | |
| 7,994,783 B2 | 8/2011 | Ledbetter et al. | |
| 8,054,074 B2 | 11/2011 | Ichihara et al. | |
| 8,212,556 B1 | 7/2012 | Schwindt et al. | |
| 8,258,884 B2 | 9/2012 | Borwick, III et al. | |
| 8,319,256 B2 | 11/2012 | Borwick, III et al. | |
| 8,334,690 B2 | 12/2012 | Kitching et al. | |
| 8,373,413 B2 | 2/2013 | Sugioka | |
| 8,405,389 B2 | 3/2013 | Sugioka et al. | |
| 8,587,304 B2 | 11/2013 | Budker et al. | |
| 8,836,327 B2 | 9/2014 | French et al. | |
| 8,906,470 B2 | 12/2014 | Overstolz et al. | |
| 8,941,377 B2 | 1/2015 | Mizutani et al. | |
| 9,095,266 B1 | 8/2015 | Fu | |
| 9,116,201 B2 | 8/2015 | Shah et al. | |
| 9,140,590 B2 | 9/2015 | Waters et al. | |
| 9,140,657 B2 | 9/2015 | Ledbetter et al. | |
| 9,169,974 B2 | 10/2015 | Parsa et al. | |
| 9,244,137 B2 | 1/2016 | Kobayashi et al. | |
| 9,291,508 B1 | 3/2016 | Biedermann et al. | |
| 9,343,447 B2 | 3/2016 | Parsa et al. | |
| 9,366,735 B2 | 6/2016 | Kawabata et al. | |
| 9,383,419 B2 | 7/2016 | Mizutani et al. | |
| 9,395,425 B2 | 7/2016 | Diamond et al. | |
| 9,417,293 B2 | 8/2016 | Schaffer et al. | |
| 9,429,918 B2 | 8/2016 | Parsa et al. | |
| 9,568,565 B2 | 2/2017 | Parsa et al. | |
| 9,575,144 B2 | 2/2017 | Komack et al. | |
| 9,601,225 B2 | 3/2017 | Parsa et al. | |
| 9,638,768 B2 | 5/2017 | Foley et al. | |
| 9,639,062 B2 | 5/2017 | Dyer et al. | |
| 9,677,905 B2 | 6/2017 | Waters et al. | |
| 9,726,626 B2 | 8/2017 | Smith et al. | |
| 9,726,733 B2 | 8/2017 | Smith et al. | |
| 9,791,536 B1 | 10/2017 | Alem et al. | |
| 9,829,544 B2 | 11/2017 | Bulatowicz | |
| 9,846,054 B2 | 12/2017 | Waters et al. | |
| 9,851,418 B2 | 12/2017 | Wolf et al. | |
| 9,869,731 B1 | 1/2018 | Hovde et al. | |
| 9,915,711 B2 | 3/2018 | Komack et al. | |
| 9,927,501 B2 | 3/2018 | Kim et al. | |
| 9,948,314 B2 | 4/2018 | Dyer et al. | |
| 9,964,609 B2 | 5/2018 | Ichihara et al. | |
| 9,964,610 B2 | 5/2018 | Shah et al. | |
| 9,970,999 B2 | 5/2018 | Larsen et al. | |
| 9,995,800 B1 | 6/2018 | Schwindt et al. | |
| 10,024,929 B2 | 7/2018 | Parsa et al. | |
| 10,088,535 B1 | 10/2018 | Shah | |
| 10,162,016 B2 | 12/2018 | Gabrys et al. | |
| 10,371,764 B2 | 8/2019 | Morales et al. | |
| 10,772,561 B2 | 9/2020 | Donaldson | |
| 2004/0232912 A1 | 11/2004 | Tsukmamoto et al. | |
| 2005/0007118 A1 | 1/2005 | Kitching et al. | |
| 2005/0046851 A1 | 3/2005 | Riley, Jr. et al. | |
| 2005/0206377 A1 | 9/2005 | Romalis et al. | |
| 2007/0120563 A1 | 5/2007 | Kawabata et al. | |
| 2007/0163367 A1 * | 7/2007 | Sherman | A61B 90/39 73/866 |
| 2007/0167723 A1 | 7/2007 | Park et al. | |
| 2007/0205767 A1 | 9/2007 | Xu et al. | |
| 2009/0079426 A1 | 3/2009 | Anderson | |
| 2009/0101806 A1 | 4/2009 | Masuda | |
| 2009/0318773 A1 | 12/2009 | Jung | |
| 2010/0219820 A1 | 9/2010 | Skidmore et al. | |
| 2011/0062956 A1 | 3/2011 | Edelstein et al. | |
| 2012/0112749 A1 | 5/2012 | Budker et al. | |
| 2013/0082700 A1 | 4/2013 | Mizutani et al. | |
| 2013/0082701 A1 | 4/2013 | Mizutani et al. | |
| 2013/0265042 A1 | 10/2013 | Kawabata et al. | |
| 2014/0306700 A1 | 10/2014 | Kamada et al. | |
| 2014/0354275 A1 | 12/2014 | Sheng et al. | |
| 2015/0022200 A1 | 1/2015 | Ichihara et al. | |
| 2015/0054504 A1 | 2/2015 | Ichihara et al. | |
| 2015/0219732 A1 * | 8/2015 | Diamond | G01R 33/16 324/201 |
| 2015/0378316 A1 | 12/2015 | Parsa et al. | |
| 2016/0061913 A1 | 3/2016 | Kobayashi et al. | |
| 2016/0116553 A1 | 4/2016 | Kim et al. | |
| 2016/0223627 A1 | 8/2016 | Shah et al. | |
| 2016/0313417 A1 | 10/2016 | Kawabata et al. | |
| 2017/0023653 A1 | 1/2017 | Kobayashi et al. | |
| 2017/0023654 A1 | 1/2017 | Kobayashi et al. | |
| 2017/0067969 A1 | 3/2017 | Butters et al. | |
| 2017/0199138 A1 | 7/2017 | Parasa et al. | |
| 2017/0261564 A1 | 9/2017 | Gabrys et al. | |
| 2017/0332933 A1 | 11/2017 | Krishnaswamy | |
| 2017/0343617 A1 | 11/2017 | Manickman et al. | |
| 2017/0343695 A1 | 11/2017 | Stetson et al. | |
| 2017/1331485 | 11/2017 | Gob et al. | |
| 2018/0003777 A1 | 1/2018 | Sorenson et al. | |
| 2018/0038921 A1 | 2/2018 | Parsa et al. | |
| 2018/0100749 A1 | 4/2018 | Waters et al. | |
| 2018/0128885 A1 | 5/2018 | Parsa et al. | |
| 2018/0156875 A1 | 6/2018 | Herbsommer et al. | |
| 2018/0219353 A1 | 8/2018 | Shah | |
| 2018/0238974 A1 | 8/2018 | Shah et al. | |
| 2018/0313908 A1 | 11/2018 | Knappe | |
| 2018/0313913 A1 | 11/2018 | DeNatale et al. | |
| 2019/0391213 A1 | 12/2019 | Alford | |
| 2020/0025844 A1 | 1/2020 | Alford et al. | |
| 2020/0057115 A1 | 2/2020 | Jimenez-Martinez et al. | |
| 2020/0057116 A1 | 2/2020 | Zorzos et al. | |
| 2020/0072916 A1 | 3/2020 | Alford et al. | |
| 2020/0088811 A1 | 3/2020 | Mohseni | |

FOREIGN PATENT DOCUMENTS

| | | | |
|---|---|---|---|
| EP | 2738627 A3 | 6/2014 | |
| EP | 200508179 B1 | 10/2015 | |

(56) References Cited

FOREIGN PATENT DOCUMENTS

| EP | 3037836 B1 | 9/2017 |
|---|---|---|
| JP | 2016109665 | 6/2016 |
| JP | 2018004462 | 1/2018 |
| WO | 2005081794 | 9/2005 |
| WO | 2014031985 | 2/2014 |
| WO | 2017095998 | 6/2017 |

OTHER PUBLICATIONS

Tim Tierney et al., "Cognitive neuroscience using wearable magnetometer arrays: Non-invasive assessment of language function", 2018 (Year: 2018).*
Elena Boto et al., "Moving magnetoencephalography towards real-world applications with a wearable system", 2018 (Year: 2018).*
Matti S. Hämäläinen, "Magnetoencephalography: A Tool For Functional Brain Imaging", Brain Topography, vol. 5. No. 2. 1992; 8 pages.
Martin W. Hess and Peter Benner, "Fast Evaluation of Time-Harmonic Maxwell's Equations Using the Reduced Basis Method", IEEE Transactions on Microwave Theory and Techniques, vol. 61, No. 6, Jun. 2013; 10 pages.
Dipankar Sarkar and N. J. Halas, "General vector basis function solution of Maxwell's equations", Physical Review E, vol. 56, No. I, Jul. 1997; 11 pages.
M. Ortner, A. Nehorai, and H. Preissl, "A spatial point process model for solving the MEG inverse problem", Washington University in St. Louis, St. Louis, Missouri, USA, University of Arkansas for Medical Sciences, Little Rock, Arkansas, USA, University of Tuebingen, Tuebingen, Germany; ELSEVIER; International Congress Series I300 (2007) 253-256; 4 pages.
Non-Final Office Action for U.S. Appl. No. 17/160,179 dated Dec. 5, 2022 38 pages.
Amendment and Response for U.S. Appl. No. 17/160,179, filed Jan. 3, 2023 26 pages.
Okada, Y.C., Lahteenmäki, A. and Xu, C., "Experimental analysis of distortion of magnetoencephalography signals by the skull." Clinical neurophysiology 110 (2), 230-238 (1999).
Robinson, J.T., Pohlmeyer, E., Gather, M.C., Kemere, C., Kitching, J.E., Malliaras, G.G., Marblestone, A., Shepard, K. L., Stieglitz, T. and Xie, C., "Developing Next-Generation Brain Sensing Technologies—A Review." IEEE sensors journal, 19(22), 10163-10175 (2019).
Shah, V., Knappe, S., Schwindt, P.D. and Kitching, J., "Subpicotesla atomic magnetometry with a microfabricated vapour cell." Nature Photon 1, 649-652 (2007).
Kitching, J., "Chip-scale atomic devices." Applied Physics Reviews, 5(3), 031302 (2018).
Hill, R.M., Boto, E., Rea, M., Holmes, N., Leggett, J., Coles, L.A., Papastavrou, M., Everton, S.K., Hunt, B.A.E., Sims, D. and Osborne J., "Multi-channel whole-head OPM-MEG: helmet design and a comparison with a conventional system." Neuroimage 219, 116995 (2020).
Griffith, W.C., Knappe, S. and Kitching, J., "Femtotesla atomic magnetometry in a microfabricated vapor cell." Optics express 18, (26), 27167-27172 (2010).
Boto, E., Holmes, N., Leggett, J., Roberts, G., Shah, V., Meyer, S.S., Muñoz, L.D., Mullinger, K.J., Tierney, T.M., Bestmann, S. and Barnes, G.R., "Moving magnetoencephalography towards real-world applications with a wearable system." Nature, 555(7698), 657-661 (2018).
Sander, T.H., Preusser, J., Mhaskar, R., Kitching, J., Trahms, L., and Knappe, S., "Magnetoencephalography with a chip-scale atomic magnetometer." Biomedical Optics Express 3, (5), 981-990 (2012).
Borna, A, Carter, T.R., Colombo, A.P., Jau, Y.Y., McKay, J., Weisend, M., Taulu, S., Stephen, J.M., and Schwindt, P.D., "Non-invasive functional-brain-imaging with an OPM-based magnetoencephalography system." Plos one 15 (1), (2020).
Kitching, J., Knappe, S., Gerginov, V., Shah, V., Schwindt, P.D., Lindseth, B., Donley E.A., "Chip-scale atomic devices: precision atomic instruments based on MEMS." In Frequency Standards And Metrology, 445-453 (2009).
Kitching, J., Knappe, S. and Donley, E.A., "Atomic sensors—a review." IEEE Sensors Journal, 11(9), 1749-1758 (2011).
Budker, D. and Romalis, M., "Optical magnetometry". Nature physics, 3(4), 227-234 (2007).
Dupont-Roc, J., Haroche, S. & Cohen-Tannoudji, C., "Detection of very weak magnetic fields (10-9 gauss) by Rb zero-field level crossing resonances", Phys. Lett. A 28, 638-639 (1969).
Happer, W., "Optical pumping", Rev. Mod. Phys., 44 (2), 169-249 (1972).
Purcell, E.M., Field, G.B., "Influence of collisions upon population of hyperfine states in hydrogen", Astrophys. J., 124, 542 (1956).
Kominis, I.K., Kornack, T.W., Allred, J.C. and Romalis, M.V., "A subfemtotesla multichannel atomic magnetometer." Nature, 422(6932), 596-599 (2003).
Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).
Bloom, A. L., "Principles of operation of the rubidium vapor magnetometer." Applied Optics 1(1), 61-68 (1962).
Bell, W.E., and Bloom, A.L., "Optically driven spin precession." Physical Review Letters 6, (6), 280 (1961).
Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment." NeuroImage, 199, 408-417 (2019).
Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).
De Cheveigné, A., Wong, D.D., Di Liberto, G.M., Hjortkjaer, J., Slaney, M. and Lalor, E., "Decoding the auditory brain with canonical component analysis." NeuroImage, 172, 206-216 (2018).
Mellinger, J., Schalk, G., Braun, C., Preissl, H., Rosenstiel, W., Birbaumer, N. and Kübler, A., "An MEG-based brain-computer interface (BCI)." Neuroimage, 36(3), 581-593 (2007).
Wolpaw, J.R., McFarland, D.J., Neat, G.W. and Forneris, C.A., "An EEG-based brain-computer interface for cursor control." Electroencephalography and clinical neurophysiology, 78(3), 252-259 (1991).
Lightfoot, G., "Summary of the N1-P2 cortical auditory evoked potential to estimate the auditory threshold in adults". Seminars in hearing, 37(1), 1 (2016).
Virtanen, J., Ahveninen, J., Ilmoniemi, R. J., Näätänen, R., & Pekkonen, E., "Replicability of MEG and EEG measures of the auditory N1/N1m-response." Electroencephalography and Clinical Neurophysiology/Evoked Potentials Section, 108(3), 291-298 (1998).
Gascoyne, L., Furlong, P. L., Hillebrand, A., Worthen, S. F., & Witton, C., "Localising the auditory N1m with event-related beamformers: localisation accuracy following bilateral and unilateral stimulation." Scientific reports, 6(1), 1-9 (2016).
Borna, A., Carter, T.R., Goldberg, J.D., Colombo, A.P., Jau, Y.Y., Berry, C., McKay, J., Stephen, J., Weisend, M. and Schwindt, P.D., "A 20-channel magnetoencephalography system based on optically pumped magnetometers." Physics in Medicine & Biology, 62(23), 8909 (2017).
Tierney, T.M., Holmes, N., Mellor, S., López, J.D., Roberts, G., Hill, R.M., Boto, E., Leggett, J., Shah, V., Brookes, M.J. and Bowtell, R., "Optically pumped magnetometers: From quantum origins to multi-channel magnetoencephalography." NeuroImage, 199, 598-608 (2019).
Iivanainen, J., Zetter, R., Grön, M., Hakkarainen, K. and Parkkonen, L., "On-scalp MEG system utilizing an actively shielded array of optically-pumped magnetometers." Neuroimage 194, 244-258 (2019).
Iivanainen, J., Stenroos, M. and Parkkonen, L., "Measuring MEG closer to the brain: Performance of on-scalp sensor arrays." NeuroImage 147, 542-553 (2017).
Allred, J, C., Lyman, R. N., Kornack, T. W., & Romalis, M. V. (2002). High-sensitivity atomic magnetometer unaffected by spin-exchange relaxation. Physical review letters, 89(13), 130801.
Balabas et al. Polarized alkali vapor with minute-long transverse spin-relaxation time, Phys. Rev. Lett. 105, Aug. 7, 2001—Published Aug. 12, 2010.

(56) References Cited

OTHER PUBLICATIONS

Barbieri, F., Trauchessec, V. Caruso, L. Trejo-Rosillo, J. Telenczuk, B. Paul E., . . . & Ouanounou, G. (2016). Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Barna, Yuan-Yu Jau, Cort N. Johnson, Amber L. Dagel, and Peter D. D. Schwindt, "Four-channel optically pumped atomic magnetometer for magnetoencephalography," Opt Express 24, 15403-15416(2016).

Dang, H.B. & Maloof, AC. & Romalis, Michael. (2009). Ultra-high sensitivity magnetic field and magnetization measurements with an atomic magnetometer. Applied Physics Letters. 97.10.1063/1.3491215.

Donley, E.A. & Hodby, E & Hollberg, L & Kitching, J. (2007). Demonstration of high-performance compact magnetic shields for chip-scale atomic devices. The Review of scientific instruments. 78.083102.

Hamalainen, Matti & Ritta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2.413-497.

Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (1 O).ISSN 2331-7019.

Jimenez-Martinez, R., Griffth, W.C., Wang, Y.J., Knappe, S., Kitching, J., Smith, K, & Prouty, M.D. (2010). Sensitivity comparison of Mix and frequency-modulated bell-bloom Cs magnetometers in a microfabricated cell. IEEE Transactions on Instrumentation and Measurement, 59(2), 372-378.

Knappe, Svenja & Sander, Tilmann & Trahms, Lutz. (2012). Optically-Pumped Magnetometers for MEG. Magnetoencephalography: From Signals to Dynamic Cortical Networks. 993-999. 10.10071978-3-642-33045-2_ 49.

Korth, H., K. Strohbehn, F. Tejada, A.G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi: 10.1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011 ). Optical rotation in excess of 100 rad generated by Rb vapor in a multipass cell. Phys. Rev. A. 84. 10.1103/PhysRevA.84.061403.

Maze, J. R., Stanwix, P. I., Hodges, J. S., Hong, S., Taylor, J.M., Cappellaro, P., . . . & Yacoby, A. (2008). Nanoscale magnetic sensing with an individual electronic spin in diamond. Nature, 455(7213), 644.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, s. J., and Romalis, M.V., "Unshielded three-axis vector operation of a spin-exchange-relaxation-free atomic magnetometer." Applied physics letters 85.20 (2004): 4804-4806.

Kiwoong Kim, Samo Begus, Hui Xia, Seung-Kyun lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014. pdf.

Sheng, Dong & R. Perry, Abigail & Krzyzewski, Sean & Geller, Shawn & Kitching, John & Knappe, Svenja. (2017). A microfabricated optically-pumped magnatic gradiometer. Applied Physics Letters. 110. 10.1063/1.4974349.

Sheng, Dehong & Li, S & Dural, Nezih & Romalis, Michael. (2013). Subfemtotesla Scalar Atomic Magoetometoy Using Multi-pass Cells. Physical review letters. 110. 160802. 10.1103/PhysRevLett.110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J. 2012. In situ triaxial magnetic field compensation for the spin-exchange-relaxation-free atomic magnetometer. Review of Scientific Instruments, 83(10), p. 103104 .

Joan Lee, Hyun & Shim, Jeong & Moon, Han Seb & Kim, Kiwoong. (2014). Flat-response spin-exchange relaxation free atomic magnetometer under negative feedback. Optics Express. 22. 10.1364/0E.22.019887.

Griffith, Clark & Jimenez-Martinez, Ricardo & Shah, Vishal & Knappe, SvenJa & Kitching, John. (2009). Miniature atomic magnetometer integrated with flux concentrators. Applied Physics Letters—Appl Phys Lett. 94. 10.105311.2885711.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.3056152.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.

Kim, Young Jin & Savukov, I. (2016). Ultra-sensitive Magnetic Microscopy with an Optically Pumped Magnetometer. Scientific Reports. 6. 24773. 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jiménez-Martinez, Dong Sheng, John LeBlanc, Lutz Trahms, Tilmann Sander, John Kitching, and Svenja Knappe, "Magnetic field imaging with microfabricated optically-pumped magnetometers," Opt Express 25, 7849-7858 (2017).

Slocum et al., Self-Calibrating Vector Magnetometer for Space, https:l/esto.nasa.gov/conferences/estc-2002/Papers/B3P4(Slocum).pdf.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

R.E. Slocum & L.J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/A0.56.005927.

Masuda, Y & Ino, T & Skoy, Vadim & Jones, G.L. (2005). 3He polarization via optical pumping in a birefringent cell. Applied Physics Letters. 87. 10.1063/1.2008370.

Larry J. Ryan, Robert E. Slocum, and Robert B. Steves, Miniature Vector Laser Magnetometer Measurements of Earth's Field, May 10, 2004, 4 pgs.

Lorenz, V.O., Dai, X., Green, H., Asnicar, T.R., & Cundiff, S.T. (2008). High-density, high temperature alkali vapor cell. Review of Scientific Instruments, 79(12), 4 pages.

F. Jackson Kimball, D & Dudley, J & Li, Y & Thulasi, Swecha & Pustelny, Szymon & Budker, Dmitry & Zoloterev, Max. (2016). Magnetic shielding and exotic spin-dependent interactions. Physical Review D. 94. 10.1103/PhysRevD.94.082005.

Huang, Haichao, et al. "Single-beam three axis atomic magnetometer." Applied Physics Letters 109.6 (2016): 062404. (Year:2016).

(56) References Cited

OTHER PUBLICATIONS

Scott Jeffrey Seltzer: "Developments in Alkali-Metal Atomic Magnetometry", Nov. 2008 (Nov. 1, 2008 ), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.

Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.

\* cited by examiner

ESTIMATING THE MAGNETIC FIELD AT DISTANCES FROM DIRECT MEASUREMENTS TO ENABLE FINE SENSORS TO MEASURE THE MAGNETIC FIELD FROM THE BRAIN USING A NEURAL DETECTION SYSTEM

RELATED APPLICATION DATA

Pursuant to 35 U.S.C. § 119(e), this application claims the benefit of U.S. Provisional Patent Application 62/975,719, filed Feb. 12, 2020, and U.S. Provisional Patent Application 63/035,664, filed Jun. 5, 2020, which are expressly incorporated herein by reference.

FIELD OF THE INVENTION

The present inventions relate to methods and systems for non-invasive measurements from the human body, and in particular, methods and systems related to detecting physiological activity from the human brain, animal brain, and/or peripheral nerves.

BACKGROUND OF THE INVENTION

Measuring neural activity in the brain is useful for medical diagnostics, neuromodulation therapies, neuroengineering, and brain-computer interfacing. Conventional methods for measuring neural activity in the brain include X-Ray Computed Tomography (CT) scans, positron emission tomography (PET), functional magnetic resonance imaging (fMRI), or other methods that are large, expensive, require dedicated rooms in hospitals and clinics, and are not wearable or convenient to use.

In contrast to these techniques, one promising technique for measuring neural activity in the brain is magnetoencephalography (MEG), which is capable of non-invasively detecting neural activity in the brain without potentially harmful ionizing radiation, and without use of heavy or large equipment. Thus, MEG-based neural activity measurement systems can be scaled to wearable or portable form factors, which is especially important in brain-computer interface (BCI) applications that require subjects to interact freely within their environment. MEG operates under the principle that time-varying electrical current within activated neurons inherently generate magnetic signals in the form of a magnetic field that can be detected by very sensitive magnetometers located around the head.

Measuring the small magnetic fields emanating from the brain, and doing so non-invasively (without surgically penetrating the skin and bone of the head) and doing so with high spatial and temporal resolution, is difficult. The magnetic fields produced by the brain are small, and they are smaller still by the time they propagate out past the skull and the skin surface of the head. In comparison, the magnetic field emitted from various outside magnetic sources in the environment, including from global sources, such as the Earth's magnetic field, and from localized sources, such as electrical outlets and sockets, electrical wires or connections in the wall, and everyday electrical equipment in a home, office, or laboratory setting, far exceed the strength of the magnetic signals generated in the brain by many orders of magnitude, and has a distribution in space and time that is not known a-priori. Hence, it is a difficult challenge to extract the small desired signal from the brain, and to discriminate it from much larger unwanted magnetic field signals from the rest of the user's natural environment.

One type of system that can be used for MEG is a Superconductive Quantum Interference Device (SQUID), which is sensitive enough to measure magnetic fields as small as $5 \times 10^{-18}$ Tesla, which can be compared to magnetic fields resulting from physiological processes in animals, which may be in the range of $10^{-9}$ to $10^{-6}$ Tesla. However, SQUIDs rely on superconducting loops, and thus require cryogenic cooling, which may make it prohibitively costly and too large to be incorporated into a wearable or portable form factor. Thus, neural activity measurement systems that utilize SQUIDs may not be appropriate for BCI applications.

Optically pumped magnetometers (OPMs) have emerged as a viable and wearable alternative to cryogenic, superconducting, SQUID-based MEG systems, and have an advantage of obviating the need for cryogenic cooling, and as a result, may be flexibly placed on any part of the body, including around the head, which is especially important for BCI applications. Because cryogenic cooling is not required, OPMs may be placed within millimeters of the scalp, thereby enabling measurement of a larger signal from the brain (brain signals dissipate with distance), especially for sources of magnetic signals at shallow depths beneath the skull, as well as providing consistency across different head shapes and sizes.

OPMs optically pump a sample (usually a vapor formed of one of the alkali metals (e.g., rubidium, cesium, or potassium) due to their simple atomic structure, low melting point, and ease of pumping with readily available lasers) with circularly polarized light at a precisely defined frequency, thereby transferring polarized light to the vapor, and producing a large macroscopic polarization in the vapor in the direction of the light (i.e., the alkali metal atoms in the vapor will all have spins that are oriented in the direction of the light) that induces a magnetically sensitive state in the vapor. Once this magnetically sensitive state is established, polarized light is no longer transferred to the vapor, but instead, passes transparently through the vapor. In the presence of an ambient magnetic field, the spin orientation (or precession) of the alkali metal atoms in the optically pumped vapor will uniformly change, thereby disrupting the magnetically sensitive state, which is then subsequently reestablished by the transfer of the polarized light to the vapor. Because the transmission of light through the vapor varies as the spin precession of the alkali metal atoms in the vapor (and thus the magnetically sensitive state) changes in response to changes in the ambient magnetic field, the transmission of light (either the pumping light or a separate probe light) through the vapor represents a magnetic field-dependent signal (i.e., a MEG signal) that may be detected, thereby providing a measure of magnitude changes in the magnetic field.

To maintain the magnetically sensitive state of the vapor, it is important that spin relaxation due to spin exchange collisions be suppressed. In low magnetic fields (<10 nT), spin relaxation due to spin exchange collisions can be suppressed greatly, and thus, some OPMs are operated as zero-field magnetometers or Spin Exchange Relaxation Free (SERF) OPMs (referred to as "SERF OPMs"), thereby allowing for very high magnetometer sensitivities. Furthermore, because OPM measurements can be quite sensitive to low-frequency noise, the polarization of the vapor may be modulated to move the MEG signal away from the low-frequency end of the spectrum. SERF OPMs typically amplitude modulate the vapor polarization using magnetic coils that generate oscillating magnetic fields that vary at a frequency (e.g., 2000 Hz) much greater than the relaxation rate of the vapor (approximately 100 Hz). The amplitude modulated MEG signal can then be demodulated using lock-in detection to recover the MEG signal.

Although SERF OPMs allow for very high magnetometer sensitivities, they have a small dynamic range and bandwidth compared to SQUIDs, and can thus only operate in small magnetic fields (tens of nT, and often lower, to stay in the linear range of the OPMs). This becomes problematic when attempting to detect a very weak neural activity-induced magnetic field from the brain against an outside magnetic field.

For example, referring to FIG. 1, the magnitude of the magnetic field generated by a human brain (i.e., the MEG signal) may range from below 5 fT to just below 1 pT, while the magnitude of the outside magnetic field, including the Earth's magnetic field, may range from just above 5 pT to 100 pT. It should be appreciated that Earth's magnetic field covers a large range as it depends on the position of the Earth, as well as the materials of the surrounding environment where the magnetic field is measured. There are also magnetic fields from electrical power lines, everyday electric objects (microwaves, fridges, cell phones), and their interaction with magnetizable objects (metal chair legs, tables, metal posts, wall rebar, etc.). In the United States these magnetic fields appear at 60 Hz and its harmonics (120 Hz, 180 Hz, etc.) and can range in amplitude from about 500 nT to below 10 nT. In Europe electrical power is at 50 Hz, with harmonics at 100 Hz, 150 Hz, etc., and similar magnitudes.

The approximate operating range of a SERF OPM (i.e., the range in which the metallic alkali vapor resonates) extends from below 1 fT up to 200 nT. Outside of this range, the metallic alkali vapor in the OPM loses sensitivity to magnetic fields. In contrast, the approximate operating range of a less sensitive sensor, such as a flux gate magnetometer, extends from around 100 fT to close to 100 pT. Thus, in contrast to flux gate magnetometers, the limited dynamic range of a SERF OPM presents a challenge in measuring signals having a high dynamic range, e.g., approximately $2 \times 10^{10}$, which corresponds to the ratio of the lower range magnitude of the MEG signal (approximately 5 fT) to the higher range magnitude of the outside magnetic field (approximately 100 µT).

Thus, to take advantage of SERF OPMs for MEG, the outside magnetic field must be suppressed to near-zero. Otherwise, the SERF OPM cannot operate. One conventional technique for suppressing the outside magnetic field involves using large, immobile, and expensive magnetically shielded rooms to passively isolate the SERF OPMs from the sources of the outside magnetic field, effectively reducing the dynamic range requirements of the SERF OPMs used to measure the weak MEG signals.

These shielded rooms, however, are generally not viable for the consumer market, especially with regard to BCI applications, where it desirable that the MEG-based neural activity measurement system be incorporated into a wearable or portable form factor. Thus, for BCI applications, SERF OPMs must be capable of operating in the ambient background magnetic field of the native environment, including the Earth's magnetic field and other local sources of magnetic fields.

Another technique for suppressing the outside magnetic field without using magnetically shielded rooms involves incorporating a direct broadband feedback control system to actively null the outside magnetic field at the SERF OPM. In this case, the system actuators attempt to cancel the entire bandwidth of the outside magnetic field by applying a noise-cancelling, broadband, magnetic field to the sensors. However, such feedback control for OPM systems has not been implemented in a wearable system.

There, thus, remains a need to provide means for more effectively suppressing an outside magnetic fields in a wearable neural detection system.

SUMMARY OF THE INVENTION

In accordance with a first aspect of the present inventions, a system comprises at least one magnetic field actuator (e.g., three orthogonal magnetic field actuators) configured for generating an actuated magnetic field that at least partially cancels an outside magnetic field, thereby yielding a total residual magnetic field. In one embodiment, each of the magnetic field actuator(s) comprises a uniform magnetic field actuator. The system further comprises a plurality of magnetometers configured for taking measurements of the total residual magnetic field. The plurality of magnetometers includes a plurality of coarse magnetometers (e.g., flux gate magnetometers) and a plurality of fine magnetometers (e.g., optically pumped magnetometers (OPMs)).

The system further comprises a processor configured for acquiring the total residual magnetic field measurements from the plurality of coarse magnetometers, and estimating the total residual magnetic field at the plurality of fine magnetometers based on total residual magnetic field measurements acquired from the plurality of coarse magnetometers.

In one embodiment, the processor is configured for estimating the total residual magnetic field at a plurality of fine magnetometers by determining a known actuated magnetic field at the plurality of magnetometers; generating a parameterized model of the outside magnetic field in the vicinity of the plurality of magnetometers based on the total residual magnetic field measurements acquired from the plurality of coarse magnetometers and the known actuated magnetic field at the plurality of coarse magnetometers; estimating the outside magnetic field at the plurality of fine magnetometers based on the parameterized outside magnetic field model (e.g., by substituting locations of the plurality of fine magnetometers into the parameterized outside magnetic field model); and estimating the total residual magnetic field at the plurality of fine magnetometers based on the known actuated magnetic field at the plurality of fine magnetometers and the outside magnetic field estimates at the plurality of fine magnetometers (e.g. by summing the known actuated magnetic field at the plurality of fine magnetometers and the outside magnetic field estimates at the plurality of fine magnetometers).

In one specific implementation of this embodiment, the processor may be configured for determining the known actuated magnetic field at the plurality of magnetometers based on a known profile of the magnetic field actuator(s) and at least one actuation strength respectively of the magnetic field actuator(s). In another specific implementation of this embodiment, the processor may be configured for generating the parameterized outside magnetic field model by generating a generic model of the outside magnetic field in the vicinity of the plurality of magnetometers, and parameterizing the generic outside magnetic field model based on the total residual magnetic field measurements acquired from the plurality of coarse magnetometers and the known actuated magnetic field at the plurality of coarse magnetometers (e.g., by fitting the generic outside magnetic field model to a difference between the total residual magnetic field measurements acquired from the plurality of coarse magnetometers and the known actuated magnetic field at the plurality of coarse magnetometers.

The generic outside magnetic field model may comprise a plurality of basis functions (e.g., $0^{th}$ order basis functions and 1st order basis functions or at least one non-linear basis function, such as, e.g., a vector spherical harmonics (VSH) basis function), in which case, the processor may be configured for fitting the generic outside magnetic field model by fitting coefficients of the plurality of basis functions to the difference between the total residual magnetic field measurements acquired from the plurality of coarse magnetometers and the known actuated magnetic field at the plurality of coarse magnetometers (e.g., using a least squares optimization technique). The processor may be configured generating the parameterized outside magnetic field model by incorporating the fitted coefficients into the generic outside magnetic field model. The processor may optionally be configured for applying Maxwell's equations to the generic outside magnetic field model in a manner that reduces the number of the plurality of basis functions.

The processor is further configured for controlling the actuated magnetic field at least partially based on the total residual magnetic field estimates at the plurality of fine magnetometers in a manner that suppresses the total residual magnetic field at the plurality of fine magnetometers to a baseline level, such that at least one of the plurality of fine magnetometers is in-range.

In one embodiment, the processor is configured for acquiring the total residual magnetic field measurement(s) from the fine magnetometer(s), estimating the total residual magnetic field at the plurality of fine magnetometers based on the total residual magnetic field measurement(s) acquired from the fine magnetometer(s), and controlling the actuated magnetic field at least partially based on the total residual magnetic field estimates at the plurality of fine magnetometers in a manner that further suppresses the total residual magnetic field at the plurality of fine magnetometers to a lower level.

In another embodiment, the processor is configured for determining whether each of the plurality of fine magnetometers is in-range or out-of-range, and assigning a weighting to each fine magnetometer based on the in-range or out-of-range determination in a manner such that the control of the actuated magnetic field at least partially based on the total residual magnetic field estimates at the plurality of fine magnetometers suppresses the total residual magnetic field at the plurality of fine magnetometers. In this embodiment, determining whether each of the plurality of fine magnetometers is in-range or out-of-range may comprise determining whether each fine magnetometer is in a linear operating range, non-linear operating range, or saturated, and the weighting may be assigned to each fine magnetometer based on the linear operating range, non-linear operating range, or saturated determination.

In still another embodiment, the system further comprises a signal acquisition unit configured for being worn on a head of a user. The signal acquisition unit comprises a support structure, the magnetic field actuator(s) affixed to the support structure, and the plurality of magnetometers affixed to the support structure. The signal acquisition unit is configured for deriving a plurality of magnetoencephalography (MEG) signals respectively from the total residual magnetic field estimates at the plurality of fine magnetometers. In this embodiment, the system further comprises a signal processing unit configured for determining an existence of neural activity in the brain of the user based on the plurality of MEG signals.

In accordance with a second aspect of the present inventions, a method comprises generating an actuated magnetic field that at least partially cancels an outside magnetic field, thereby yielding a total residual magnetic field. In one method, the actuated magnetic field is generated in three orthogonal directions. In another method, the actuated magnetic field is uniform.

The method further comprises acquiring measurements of the total residual magnetic field respectively from a plurality of detection locations, and in particular, coarse total residual magnetic field measurements are acquired from a first set of the plurality of detection locations, and fine total residual magnetic field measurements are acquired from a second set of the plurality of detection locations.

The method further comprises estimating the total residual magnetic field at the second set of detection locations based on the coarse total residual magnetic field measurements acquired from the first set of detection locations.

In one method, estimating the total residual magnetic field at the second set of detection locations comprises determining a known actuated magnetic field at the plurality of detection locations; generating a parameterized model of the outside magnetic field model in the vicinity of the plurality of detection locations based on the coarse total residual magnetic field measurements acquired from the first set of detection locations and the known actuated magnetic field at the first set of detection locations; estimating the outside magnetic field at the second set of detection locations based on the parameterized outside magnetic field model (e.g., by substituting the second set of detection locations into the parameterized outside magnetic field model into the parameterized outside magnetic field model); and estimating the total residual magnetic field at the second set of detection locations based on the known actuated magnetic field at the second set of detection locations and the outside magnetic field estimates at the second set of detection locations (e.g. by summing the known actuated magnetic field at the second set of detection locations and the outside magnetic field estimates at the second set of detection locations).

In one specific implementation of this method, the known actuated magnetic field at the plurality of detection locations may be determined based on a known profile of the actuated magnetic field and actuation strength of the actuated magnetic field. In another specific implementation of this method, generating the parameterized outside magnetic field model comprises generating a generic model of the outside magnetic field in the vicinity of the plurality of detection locations, and parameterizing the generic outside magnetic field model based on the total residual magnetic field measurements acquired from the first set of detection locations and the known actuated magnetic field at the first set of detection locations (e.g., by fitting the generic outside magnetic field model to a difference between the coarse total residual magnetic field measurements acquired from the first set of detection locations and the known actuated magnetic field at the first set of detection locations).

The generic outside magnetic field model may comprise a plurality of basis functions (e.g., $0^{th}$ order basis functions and 1st order basis functions or at least one non-linear basis function, such as, e.g., a vector spherical harmonics (VSH) basis function), in which case, fitting the generic outside magnetic field model may comprise fitting coefficients of the plurality of basis functions to the difference between the coarse total residual magnetic field measurements acquired from the first set of detection locations and the known actuated magnetic field at the first set of detection locations (e.g., using a least squares optimization technique). Generation of the parameterized outside magnetic field model may comprise incorporating the fitted coefficients into the generic outside magnetic field model. The method may optionally comprise applying Maxwell's equations to the generic outside magnetic field model in a manner that reduces the number of the plurality of basis functions.

The method further comprises controlling the actuated magnetic field at least partially based on the total residual magnetic field estimates at the second set of detection locations in a manner that suppresses the total residual magnetic field at the second set of detection locations to a baseline level, such that an accuracy of at least one of the fine total residual magnetic field measurements acquired from at least one of the second set of detection locations increases.

One method further comprises deriving a plurality of magnetoencephalography (MEG) signals respectively from the total residual magnetic field estimates at the second set of detection locations, and determining an existence of neural activity in the brain of a user based on the plurality of MEG signals.

Another method further comprises acquiring the fine total residual magnetic field measurement(s) from at least one of the second set of detection location, estimating the total residual magnetic field at the second set of detection locations based on the total residual magnetic field measurement(s) acquired from at least one of the second set of detection location, and controlling the actuated magnetic field at least partially based on the total residual magnetic field estimates at the second set of detection locations in a manner that further suppresses the total residual magnetic field at the second set of detection locations to a lower level, such that the accuracy of the fine total residual magnetic field measurement(s) acquired from at least one of the second set of detection locations increases.

Still another method further comprises determining an accuracy of each of the fine total residual magnetic field measurements acquired from the second set of detection locations, and assigning a weighting to the each fine total residual magnetic field measurement based on the accuracy determination in a manner such that the control of the actuated magnetic field at least partially based on the total residual magnetic field estimates at the second set of detection locations suppresses the total residual magnetic field at the second set of detection locations.

In accordance with a third aspect of the present inventions, a system comprises at least one magnetic field actuator (e.g., three orthogonal magnetic field actuators) configured for generating an actuated magnetic field that at least partially cancels an outside magnetic field, thereby yielding a total residual magnetic field. In one embodiment, each of the magnetic field actuator(s) comprises a uniform magnetic field actuator. The system further comprises a plurality of magnetometers configured for taking measurements of the total residual magnetic field. The plurality of magnetometers includes a plurality of coarse magnetometers (e.g., flux gate magnetometers) and a plurality of fine magnetometers (e.g., optically pumped magnetometers (OPMs)).

The system further comprises a processor configured for acquiring the total residual magnetic field measurements from a first set of the plurality of magnetometers, and estimating the total residual magnetic field at a second set of the plurality of magnetometers based on total residual magnetic field measurements acquired from the first set of magnetometers, and controlling the actuated magnetic field at least partially based on the total residual magnetic field estimates at the second set of magnetometers.

In one embodiment, each of the first set of magnetometers is an in-range magnetometer, and at least one of the second set of magnetometers is an out-of-range magnetometer. In another embodiment, each of the second set of magnetometers is an out-of-range magnetometer. In still another embodiment, at least one of the second set of magnetometers is an in-range magnetometer. In yet another embodiment, the first set of magnetometers and the second set of magnetometers comprises at least one common magnetometer. In yet another embodiment, all of the first set of magnetometers and all of the second set of magnetometers are common. In yet another embodiment, at least one of the first set of magnetometers is a coarse magnetometer (e.g., a flux gate magnetometer), and wherein at least one of the second set of magnetometers is a fine magnetometer (e.g., an optically pumped magnetometer (OPM)).

In another embodiment, the processor is configured for estimating the total residual magnetic field at the second set of magnetometers by determining a known actuated magnetic field at the plurality of magnetometers; generating a parameterized model of the outside magnetic field in the vicinity of the plurality of magnetometers based on the total residual magnetic field measurements acquired from the first set of magnetometers and the known actuated magnetic field at the first set of coarse magnetometers; estimating the outside magnetic field at the second set of magnetometers based on the parameterized outside magnetic field model (e.g., by substituting locations of second set of magnetometers into the parameterized outside magnetic field model); and estimating the total residual magnetic field at the second set of magnetometers based on the known actuated magnetic field at the second set of magnetometers and the outside magnetic field estimates at the second set of magnetometers (e.g. by summing the known actuated magnetic field at the second set of magnetometers and the outside magnetic field estimates at the second set of magnetometers).

In one specific implementation of this embodiment, the processor may be configured for determining the known actuated magnetic field at the plurality of magnetometers based on a known profile of the magnetic field actuator(s) and at least one actuation strength respectively of the magnetic field actuator(s). In another specific implementation of this embodiment, the processor may be configured for generating the parameterized outside magnetic field model by generating a generic model of the outside magnetic field in the vicinity of the plurality of magnetometers, and parameterizing the generic outside magnetic field model based on the total residual magnetic field measurements acquired from the first set of magnetometers and the known actuated magnetic field at the first set of magnetometers (e.g., by fitting the generic outside magnetic field model to a difference between the total residual magnetic field measurements acquired from the first set of magnetometers and the known actuated magnetic field at the plurality of first set of magnetometers.

The generic outside magnetic field model may comprise a plurality of basis functions (e.g., $0^{th}$ order basis functions and 1st order basis functions or at least one non-linear basis function, such as, e.g., a vector spherical harmonics (VSH) basis function), in which case, the processor may be configured for fitting the generic outside magnetic field model by fitting coefficients of the plurality of basis functions to the difference between the total residual magnetic field measurements acquired from the first set of magnetometers and the known actuated magnetic field at the first set of magnetometers (e.g., using a least squares optimization technique). The processor may be configured generating the parameterized outside magnetic field model by incorporating the fitted coefficients into the generic outside magnetic field model. The processor may optionally be configured for applying Maxwell's equations to the generic outside magnetic field model in a manner that reduces the number of the plurality of basis functions.

In accordance with a fourth aspect of the present inventions, a method comprises generating an actuated magnetic field that at least partially cancels an outside magnetic field, thereby yielding a total residual magnetic field. In one method, the actuated magnetic field is generated in three orthogonal directions. In another method, the actuated magnetic field is uniform.

The method further comprises acquiring measurements of the total residual magnetic field respectively from a first set of detection locations, estimating the total residual magnetic field at the second set of detection locations based on the total residual magnetic field measurements acquired from the first set of detection locations, and controlling the actuated magnetic field at least partially based on the total residual magnetic field estimates at the second set of detection locations. In one method, the first set of detection locations and the second set of detection locations comprises at least one common detection location. In another method, all of the first set of detection locations and all of the second set of detection locations are common.

In one method, estimating the total residual magnetic field at the second set of detection locations comprises determining a known actuated magnetic field at the plurality of detection locations; generating a parameterized model of the outside magnetic field model in the vicinity of the plurality of detection locations based on the total residual magnetic field measurements acquired from the first set of detection locations and the known actuated magnetic field at the first set of detection locations; estimating the outside magnetic field at the second set of detection locations based on the parameterized outside magnetic field model (e.g., by substituting the second set of detection locations into the parameterized outside magnetic field model into the parameterized outside magnetic field model); and estimating the total residual magnetic field at the second set of detection locations based on the known actuated magnetic field at the second set of detection locations and the outside magnetic field estimates at the second set of detection locations (e.g. by summing the known actuated magnetic field at the second set of detection locations and the outside magnetic field estimates at the second set of detection locations).

In one specific implementation of this method, the known actuated magnetic field at the plurality of detection locations may be determined based on a known profile of the actuated magnetic field and actuation strength of the actuated magnetic field. In another specific implementation of this method, generating the parameterized outside magnetic field model comprises generating a generic model of the outside magnetic field in the vicinity of the plurality of detection locations, and parameterizing the generic outside magnetic field model based on the total residual magnetic field measurements acquired from the first set of detection locations and the known actuated magnetic field at the first set of detection locations (e.g., by fitting the generic outside magnetic field model to a difference between the total residual magnetic field measurements acquired from the first set of detection locations and the known actuated magnetic field at the first set of detection locations).

The generic outside magnetic field model may comprise a plurality of basis functions (e.g., $0^{th}$ order basis functions and 1st order basis functions or at least one non-linear basis function, such as, e.g., a vector spherical harmonics (VSH) basis function), in which case, fitting the generic outside magnetic field model may comprise fitting coefficients of the plurality of basis functions to the difference between the coarse total residual magnetic field measurements acquired from the first set of detection locations and the known actuated magnetic field at the first set of detection locations (e.g., using a least squares optimization technique). Generation of the parameterized outside magnetic field model may comprise incorporating the fitted coefficients into the generic outside magnetic field model. The method may optionally comprise applying Maxwell's equations to the generic outside magnetic field model in a manner that reduces the number of the plurality of basis functions.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the present inventions and are not therefore to be considered limiting of its scope, the present inventions will be described and explained with additional specificity and detail through the use of the accompanying drawings in which.

DETAILED DESCRIPTION OF THE EMBODIMENTS

Significantly, the neural activity measurement systems (and variations thereof) described herein are configured for non-invasively acquiring magnetoencephalography (MEG) signals from a brain of a user while effectively suppressing an outside magnetic field without the use of magnetically shielded rooms, and identifying and localizing the neural activity within the cortical structures of the brain of the user based on the acquired magnetoencephalography (MEG) signals.

The neural activity measurement system described herein may take the form of a brain computer interface (BCI) (also known as a neural-controlled interface (NCI), mind-machine interface (MMI), direct neural interface (DNI), or brain-machine interface (BMI)), which converts the neural activity information into commands that are output to an external device or devices for carrying out desired actions that replace, restore, enhance, supplement, or improve natural central nervous system (CNS) output, and thereby changes the ongoing interactions between the CNS of a user and an external or internal environment.

Figure 1:
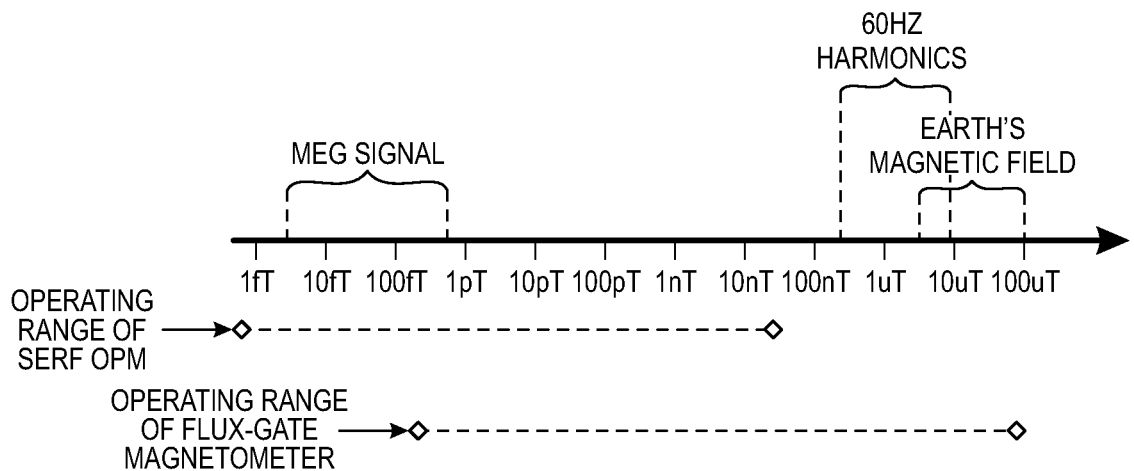
FIG. 1 is a diagram of illustrating dynamic ranges of a magnetoencephalography (MEG) signal and a typical outside magnetic field, and the operating ranges of a Spin Exchange Relaxation Free (SERF) optically-pumped magnetometer (OPM) and flux gate magnetometer, plotted on a magnetic spectrum.
Figure 2:
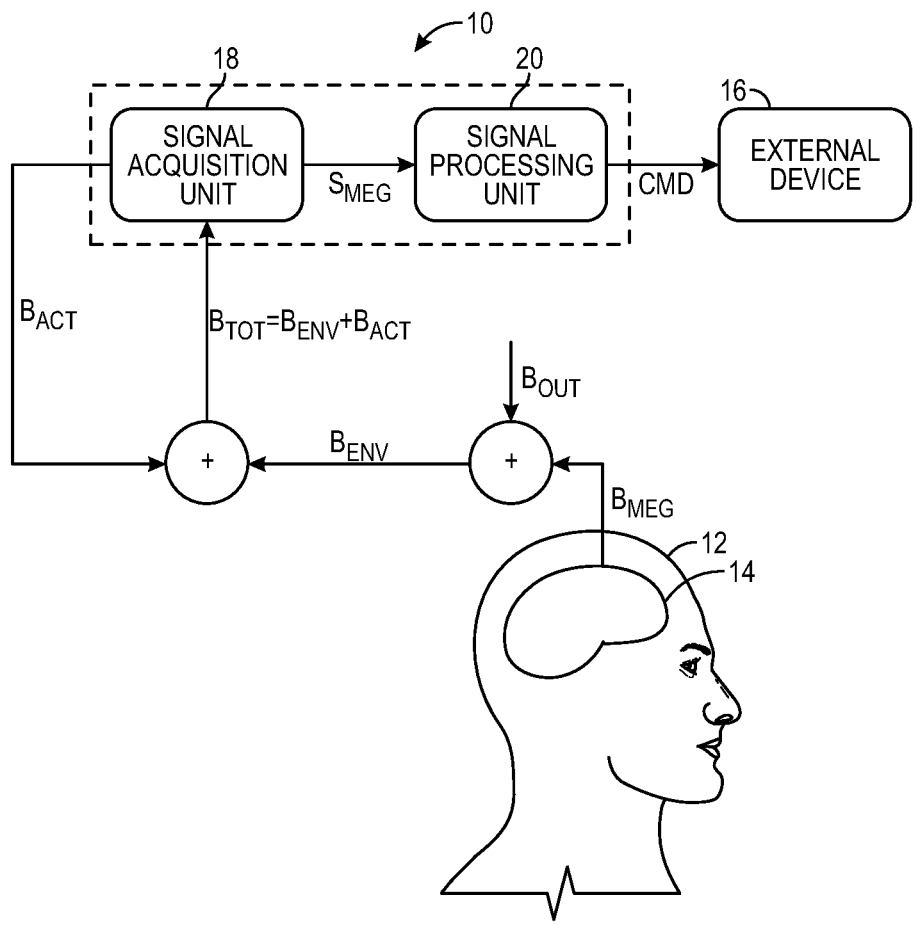
FIG. 2 is a block diagram of a neural activity measurement system constructed in accordance with one embodiment of the present inventions, particularly shown in the context of a brain computer interface (BCI.

For example, as illustrated in FIG. 2, one embodiment of a neural activity measurement system 10 constructed in accordance with the present inventions will be described. The neural activity measurement system 10 is configured for measuring neural activity in the brain 14 of a user 12, generating commands CMD in response to the measured neural activity information, and sending the commands CMD to an external device 16 in the context of a BCI.

To this end, the neural activity measurement system 10 generally comprises a signal acquisition unit 18 configured for at least partially cancelling a relatively strong outside magnetic field $B_{OUT}$ within an environmental magnetic field $B_{ENV}$ that also includes a relatively weak MEG magnetic field $B_{MEG}$ induced by electrical current (indicative of neural activity) in a brain 14 of a user 12. That is, $B_{TOT}=B_{ENV}+B_{ACT}=B_{OUT}+B_{MEG}+B_{ACT}$. The outside magnetic field $B_{OUT}$ may emanate from global sources (e.g., the Earth's magnetic field), and from localized sources, including, but not limited to, from electromagnetic radiation emanating from electrical outlets and sockets, electrical wires or connections in the wall, and everyday electrical equipment (microwave ovens, televisions, refrigerators, environmental systems (air conditioning, etc.) in a home, office, or laboratory setting, as well as from cell phones, biomagnetics unrelated to neural signals (such as facial muscles, magnetic fields produced by the heart or nerves firing), everyday objects encountered inside (metal and magnetic objects, including steel supports, rebar, studs, utility boxes, etc.) and outside spaces, such as cell phone towers, power lines, transformers, and moving vehicles (e.g., cars, trains, bikes, electric bikes and scooters, electric cars, etc.), user motion/rotation/translation in a background field (earth field), user clothing and eyeglasses, personal electronics (e.g., laptop computers, watches, phones, smart rings, etc.), active implantable medical devices (pacemakers), augmented reality/virtual reality, sound systems (that use magnets), etc.

The signal acquisition unit 18 is configured for generating an actuated magnetic field $B_{ACT}$ that at least partially cancels the relative strong outside magnetic field $B_{OUT}$ within the environmental magnetic field $B_{ENV}$, yielding a total residual magnetic field $B_{TOT}$ (which is preferably zero or near-zero due to the summation of the environmental magnetic field $B_{ENV}$ and the actuated magnetic field $B_{ACT}$. The signal acquisition unit 18 is further configured for detecting the total residual magnetic field $B_{TOT}$ as feedback to cancel the outside magnetic field $B_{OUT}$. The signal acquisition unit 18 is also configured for extracting and outputting a clean (i.e., reduced-noise) electrical MEG signals $S_{MEG}$ of the MEG magnetic field $B_{MEG}$ from the total residual magnetic field $B_{TOT}$.

The signal acquisition unit 18 may utilize any suitable technique for acquiring the MEG magnetic field $B_{MEG}$, including, but not limited to the techniques described in U.S. patent application Ser. No. 16/428,871, entitled "Magnetic Field Measurement Systems and Methods of Making and Using," U.S. patent application Ser. No. 16/418,478, entitled "Magnetic Field Measurement System and Method of Using Variable Dynamic Range Optical Magnetometers", U.S. patent application Ser. No. 16/418,500, entitled, "Integrated Gas Cell and Optical Components for Atomic Magnetometry and Methods for Making and Using," U.S. patent application Ser. No. 16/457,655, entitled "Magnetic Field Shaping Components for Magnetic Field Measurement Systems and Methods for Making and Using," U.S. patent application Ser. No. 16/213,980, entitled "Systems and Methods Including Multi-Mode Operation of Optically Pumped Magnetometer(s)," (now U.S. Pat. No. 10,627,460), U.S. patent application Ser. No. 16/456,975, entitled "Dynamic Magnetic Shielding and Beamforming Using Ferrofluid for Compact Magnetoencephalography (MEG)," U.S. patent application Ser. No. 16/752,393, entitled "Neural Feedback Loop Filters for Enhanced Dynamic Range Magnetoencephalography (MEG) Systems and Methods," U.S. patent application Ser. No. 16/741,593, entitled "Magnetic Field Measurement System with Amplitude-Selective Magnetic Shield," U.S. Provisional Application Ser. No. 62/858,636, entitled "Integrated Magnetometer Arrays for Magnetoencephalography (MEG) Detection Systems and Methods," U.S. Provisional Application Ser. No. 62/836,421, entitled "Systems and Methods for Suppression of Non-Neural Interferences in Magnetoencephalography (MEG) Measurements," U.S. Provisional Application Ser. No. 62/842,818 entitled "Active Shield Arrays for Magnetoencephalography (MEG)," U.S. Provisional Application Ser. No. 62/926,032 entitled "Systems and Methods for Multiplexed or Interleaved Operation of Magnetometers," U.S. Provisional Application Ser. No. 62/896,929 entitled "Systems and Methods having an Optical Magnetometer Array with Beam Splitters," and U.S. Provisional Application Ser. No. 62/960,548 entitled "Methods and Systems for Fast Field Zeroing for Magnetoencephalography (MEG)," which are all expressly incorporated herein by reference.

The neural activity measurement system 10 further comprises a signal processing unit 20 configured for processing the electrical MEG signal $S_{MEG}$ to identify and localize neural activity within the cortex of the brain 14 of the user 12, and issuing the commands CMD to the external device 16 in response to the identified and localized neural activity in the brain 14 of the user 12.

It should be appreciated that, although the neural activity measurement system 10 is described herein in the context of a BCI, the present inventions should not be so limited, and may be applied to any system used for any application (including, but not limited to, medical, entertainment, neuromodulation stimulation, lie detection devices, alarm, educational, etc.), where it is desirable to perform measurements on a magnetic field induced by any physiological process in a person that would benefit from cancelling the outside magnetic field $B_{OUT}$. For example, instead of deriving neural activity information from MEG signals, magnetic fields induced by electrical heart activity can be measured to determine heart activity information of a person.

Furthermore, it should also be appreciated that, although the use of the signal acquisition unit lends itself well to neural activity measurement systems, the signal acquisition unit 18 may find use in other applications, such as, e.g., other types of biomedical sensing, vehicle navigation, mineral exploration, non-destructive testing, detection of underground devices, asteroid mining, space exploration, etc. Thus, signal acquisition unit 18 can be adapted to measure neural signals generated from non-brain anatomical structures, as well as other types of biological signals and non-biological signals.

Figure 3:
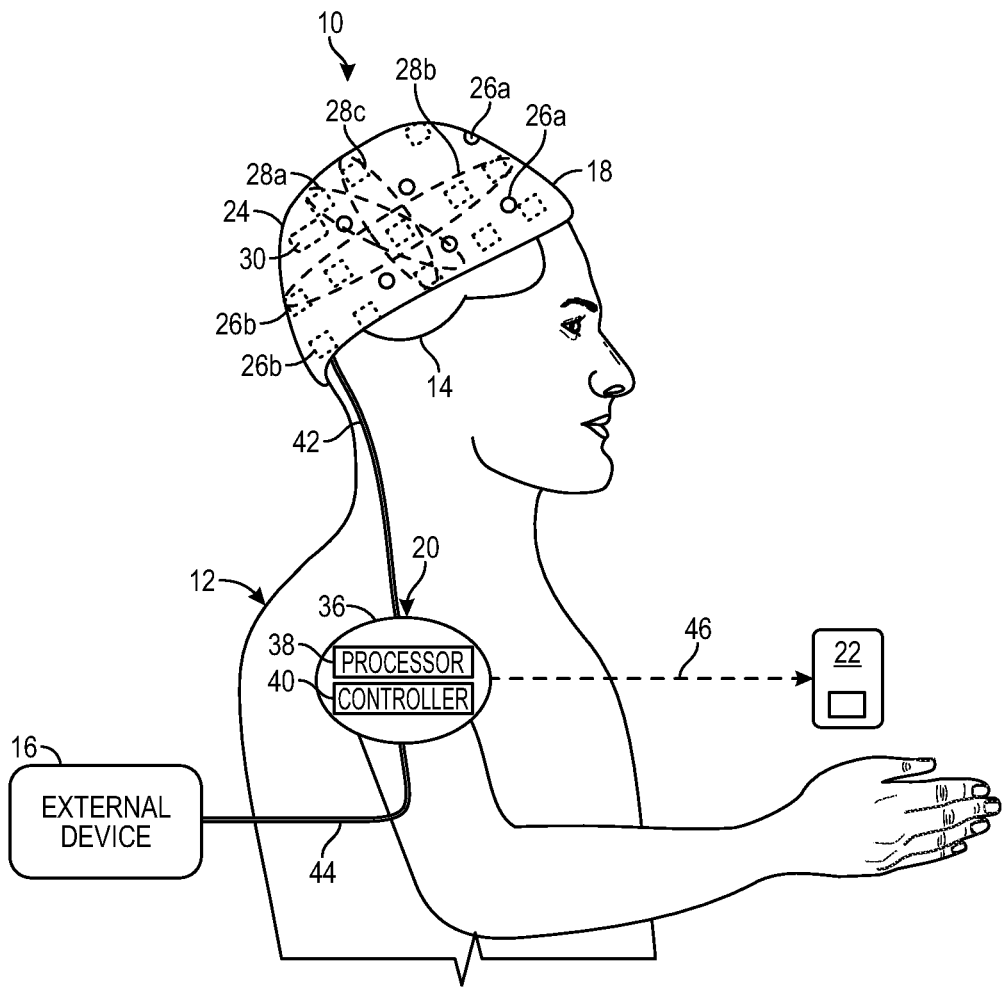
FIG. 3 is a side view of a physical implementation of the BCI of FIG. 3.

Referring now to FIG. 3, an exemplary physical implementation of the neural activity measurement system 10 will be described.

As shown, the signal acquisition unit 18 is configured for being applied to the user 12, and in this case, worn on the head of the user 12. The signal acquisition unit 18 comprises a support structure 24, a plurality of magnetometers 26 (divided between a plurality of coarse magnetometers 26a and a plurality of fine magnetometers 26b) distributed about the support structure 24, a set of magnetic field actuators 28 in proximity to the fine magnetometers 26b, and a processor 30 electrically coupled between the magnetometers 26 and the set of actuators 28.

The support structure 24 may be shaped, e.g., have a banana, headband, cap, helmet, beanie, other hat shape, or other shape adjustable and conformable to the user's head, such that at least some of the magnetometers 26 are in close proximity, preferably in contact, with the outer skin of the head, and in this case, the scalp of the user 12. The support structure 24 may be made out of any suitable cloth, soft polymer, plastic, hard shell, and/or any other suitable material as may serve a particular implementation. An adhesive, strap, or belt (not shown) can be used to secure the support structure 24 to the head of the user 12.

Each of the magnetometers 26 is configured for detecting a spatial component of the total residual magnetic field $B_{TOT}$, and outputting a corresponding electrical signal representative of the spatial component of the total residual magnetic field $B_{TOT}$. In the illustrated embodiment, the plurality of coarse magnetometers 26a is distributed on the outside of the support structure 24 for detecting the respective spatial components of the total residual magnetic field $B_{TOT}$ mainly from outside of the support structure 24, whereas the plurality of fine magnetometers 26b is distributed on the inside of the support structure 24 for detecting the respective spatial components of the total residual magnetic field $B_{TOT}$ mainly from inside the support structure 24 (i.e. they are closer to the brain 14 of the user 12).

Each of the coarse magnetometers 26a has a relatively low sensitivity, but high dynamic sensitivity range, to magnetic fields, whereas each of the fine magnetometers 26b has a relatively high sensitivity, but low dynamic sensitivity range. The signal acquisition unit 18 may have any suitable number of magnetometers 26. For example, the signal acquisition unit 18 may have twelve coarse magnetometers 26a and twenty-five fine magnetometers 26b, although one of ordinary skill in the art would understand that signal acquisition unit 18 may have any suitable number of coarse magnetometers 26a and magnetometers 26b, including more coarse magnetometers 26a then fine magnetometers 26b. In alternative embodiments of the signal acquisition unit 18, the plurality of magnetometers 26 may only comprise a plurality of fine magnetometers 26b distributed on the inside of the support structure 24.

In the illustrated embodiment, each coarse magnetometer 26a takes the form of a flux gate magnetometer, which has a relatively low sensitivity (e.g., on the order of 100 fT), and thus, may not be capable of measuring weak magnetic fields generated by neural activity in the brain 14 of the user 12. However, a flux gate magnetometer has a relatively high dynamic sensitivity range (in the range of 100 fT to close to 100 pT), and thus, may operate in a large outside magnetic field $B_{OUT}$. Although each of the coarse magnetometers 26a are described as taking the form of a flux gate magnetometer, other types of coarse magnetometers can be used, including, but not limited to, anisotropic magnetoresistance (AMR) sensors, tunnel magnetoresistance (TMR) sensors, Hall-effect sensors, nitrogen vacancy sensors, or any other magnetometer that can operate in a linear range over the amplitude range of a typical outside magnetic field $B_{OUT}$. As will be described in further detail below, each of the coarse magnetometers 26a is specifically designed to facilitate the calibration of its offset and gain using novel pre-calibration and dynamic calibration techniques.

In the illustrated embodiment, each fine magnetometer 26b takes the form of a Spin Exchange Relaxation Free (SERF) Optically Pumped Magnetometer (OPM). Although a SERF OPM has a relatively small dynamic range (e.g., in the range of 1 ft to 200 nT), it has a relatively high sensitivity (on the order of 1 fT) to magnetic fields compared to flux gate magnetometers. Further details of SERF OPMs are described in U.S. Provisional Application Ser. No. 62/975,693, entitled "Nested and Parallel Feedback Control Loops For Ultra-Fine Measurements of Magnetic Fields From the Brain Using a Wearable MEG System", which is expressly incorporated herein by reference.

The clean (i.e., reduced-noise) electrical MEG signals $S_{MEG}$ that are representative of the spatial components of the MEG magnetic field $B_{MEG}$, and that will be processed by the signal processing unit 20 for determining and localizing neural activity in the brain 14 of the user 12, will be respectively derived from the electrical signals output by the respective fine magnetometers 26b, and in some cases, from the electrical signals output by the coarse magnetometers 26a; whereas the characteristics (namely amplitude and phase) of the actuated magnetic field $B_{ACT}$ will be derived from the electrical signals output by the respective coarse magnetometers 26a and/or the electrical signals output by at least some of the respective fine magnetometers 26b.

The set of magnetic field actuators 28 is configured for generating the actuated magnetic field $B_{ACT}$ to at least partially cancel the outside magnetic field $B_{OUT}$ in the vicinity of the plurality of fine magnetometers 26b. The set of magnetic field actuators 28 may, e.g., comprise at least one coil and at least one driver that drives the coil(s) with electrical current at a defined amperage, voltage, or some other variable, and at a defined frequency, thereby setting the actuation strengths of the magnetic field actuators 28. In the illustrated embodiment, the set of magnetic field actuators 28 comprises a triad of uniform magnetic field actuators 28a-28c for respectively generating x-, y-, and z-components of the actuated magnetic field $B_{ACT}$ to cancel the outside magnetic field $B_{OUT}$ in all three dimensions. In an optional embodiment, the set of magnetic field actuators 28 may also comprise six gradient magnetic field actuators (not shown) for generating first-order x-, y-, and z-gradient components of the actuated magnetic field $B_{ACT}$. One of ordinary skill in the art would appreciate that the set of field actuators 28 may include any suitable and type of magnetic field actuators capable of cancelling the outside magnetic field $B_{OUT}$ at the magnetometers 26.

The processor 30 is electrically coupled between the magnetometers 26 and magnetic field actuators 28 via electrical wires (not shown), and is configured for processing the electrical signals respectively output by the coarse magnetometers 26a (and in some cases the electrical signals output by the fine magnetometers 26b) in response to the detection of the spatial components of the total residual magnetic field $B_{TOT}$, determining the characteristics of the actuated magnetic field $B_{ACT}$ required to cancel the outside magnetic field $B_{OUT}$ in the total residual magnetic field $B_{TOT}$, and generating noise-cancelling control signals based on this determination that are output to the set of magnetic field actuators 28.

Further details discussing novel techniques for cancelling the outside magnetic field $B_{OUT}$ in the total residual magnetic field $B_{TOT}$ are described in U.S. Provisional Application Ser. No. 62/975,693, entitled "Nested and Parallel Feedback Control Loops For Ultra-Fine Measurements of Magnetic Fields From the Brain Using a Wearable MEG System". Significantly, as will be described in further detail below, the processor 30 is also configured for estimating the total residual magnetic field $B_{TOT}$ at the fine magnetometers 26a (and optionally the coarse magnetometers 26a) based on measurements of the total residual magnetic field $B_{TOT}$ taken by the coarse magnetometers 26a (and optionally the fine magnetometers 26b) for purposes of more accurately cancelling the outside magnetic field $B_{OUT}$.

To minimize the size, weight, and cost of the signal acquisition unit 18, the functions of the processor 30 are preferably performed digitally (e.g., in firmware, such as a programmable logic device (e.g., a field programmable gate array (FPGA), or an ASIC (application specific integrated circuit) device, or in a micro-processor)), in which case, one or more analog-to-digital converters (not shown) can be employed between the magnetometers 26 and the processor 30, and one or more digital-to-analog converters (not shown) can be employed between the magnetic field actuators 28 and the processor 30. However, it should be appreciated that, in alternative embodiments, the functions of the processor 30 may be at least partially performed in an analog fashion.

It should be noted that, although the signal acquisition unit 18 is illustrated in FIG. 3 as having a single set of magnetic field actuators 28 and a single processor 30, the signal acquisition unit 18 may comprise more than one set of magnetic field actuators 28 and more than one processor 30. In this case, each set of magnetic field actuators 28 and each corresponding processor 30 may be associated with a set of magnetometers 26. In one embodiment, the fine magnetometers 26b, set(s) of magnetic field actuators 28, and processor(s) 30 may be fabricated as integrated module(s). For example, each integrated module may comprise a rectangular substrate containing a set or all of the fine magnetometers 26b, a set of the magnetic field actuators 28 incorporated into the rectangular substrate, such that coils of the magnetic field actuators 28 respectively wrap around the orthogonal dimensions of the rectangular substrate, and the processor 30 affixed to the surface of the rectangular substrate between the coils.

The signal processing unit 20 is configured for being applied to the user 12, and in this case, worn remotely from the head of the user 12, e.g., worn on the neck, shoulders, chest, or arm) of the user 12. The signal processing unit 20 comprises a housing 36 containing its own processor 38 and a controller 40. The processor 38 is configured for identifying and localizing neural activity within the cortex of the brain 14 of the user 12, and the controller 40 is configured for issuing commands CMD to an external device 16 in response to the identified and localized neural activity in the brain 14 of the user 12, as well as controlling the high-level operational functions of the signal acquisition unit 18. The signal processing unit 20 may additionally include a power supply (which if head-worn, may take the form of a rechargeable or non-chargeable battery), a control panel with input/output functions, a display, and memory. Alternatively, power may be provided to the signal processing unit 20 wirelessly (e.g., by induction).

In the illustrated embodiment, the neural activity measurement system 10 further comprises a wired connection 42 (e.g., electrical wires) for providing power from the signal processing unit 20 to the signal acquisition unit 18 and communicating between the signal processing unit 20 and the signal acquisition unit 18. Alternatively, the neural activity measurement system 10 may use a non-wired connection (e.g., wireless radio frequency (RF) signals (e.g., Bluetooth, Wifi, cellular, etc.) or optical links (e.g., fiber optic or infrared (IR)) for providing power from the signal processing unit 20 to the signal acquisition unit 18 and/or communicating between the signal processing unit 20 and the signal acquisition unit 18.

In the illustrated embodiment, the neural activity measurement system 10 further comprises a wired connection 44 (e.g., electrical wires) for providing power from the signal processing unit 20 to the external device 16 and communicating between the signal processing unit 20 and the external device 16. Alternatively, the neural activity measurement system 10 may use a non-wired connection (e.g., wireless radio frequency (RF) signals (e.g., Bluetooth, Wifi, cellular, etc.) or optical links (e.g., fiber optic or infrared (IR)) for providing power from the signal processing unit 20 to the external device 16 and/or communicating between the signal processing unit 20 and the external device 16.

The neural activity measurement system 10 may optionally comprise a remote processor 22 (e.g., a Smartphone, tablet computer, or the like) in communication with the signal processing unit 20 coupled via a wired connection (e.g., electrical wires) or a non-wired connection (e.g., wireless radio frequency (RF) signals (e.g., Bluetooth, Wifi, cellular, etc.) or optical links (e.g., fiber optic or infrared (IR)) 46. The remote processor 22 may store data from previous sessions, and include a display screen.

It should be appreciated that at least a portion of the signal acquisition and magnetic field cancellation functionality of the processor 30 in the signal acquisition unit 18 may be implemented in the signal processing unit 20, and/or at least a portion of the neural activity determination and localization functionality of the signal processing unit 20 may be implemented in the signal acquisition unit 18. In the preferred embodiment, the functionalities of the processor 30 in the signal acquisition unit 18, as well as the processor 38 and a controller 40 in the signal processing unit 20, may be implemented using one or more suitable computing devices or digital processors, including, but not limited to, a microcontroller, microprocessor, digital signal processor, graphical processing unit, central processing unit, application specific integrated circuit (ASIC), field programmable gate array (FPGA), and/or programmable logic unit (PLU). Such computing device(s) or digital processors may be associated with non-transitory computer- or processor-readable medium that stores executable logic or instructions and/or data or information, which when executed, perform the functions of these components. The non-transitory computer- or processor-readable medium may be formed as one or more registers, for example of a microprocessor, FPGA, or ASIC, or can be a type of computer-readable media, namely computer-readable storage media, which may include, but is not limited to, RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The signal acquisition unit 18 takes advantage of the high dynamic range of the coarse magnetometers 26a to compensate for the relatively low dynamic range of the fine magnetometers 26b to cancel the large outside magnetic field $B_{OUT}$, while also taking advantage of high sensitivity of the fine magnetometers 26b to compensate for the low sensitivity of the coarse magnetometers 26a to measure the MEG signal $S_{MEG}$.

Figure 4:
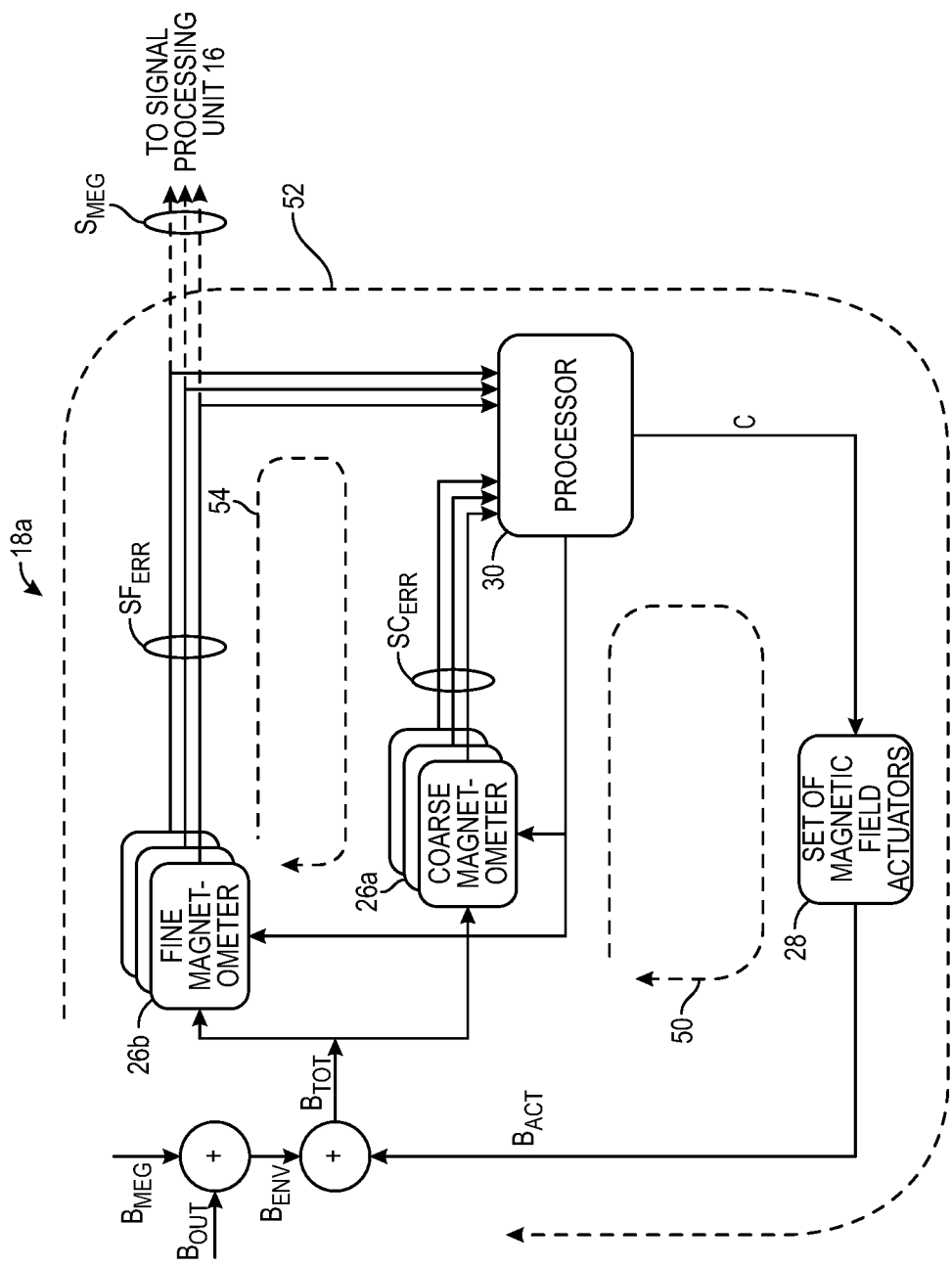
FIG. 4 is a block diagram of one exemplary embodiment of a signal acquisition unit used by the neural activity measurement system of FIG. 2.

In particular, and with reference to FIG. 4, the signal acquisition unit 18 is configured for at least partially cancelling the outside magnetic field $B_{OUT}$ in the total residual magnetic field $B_{TOT}$ at the locations of the fine magnetometers 26b by initially employing a coarse feedback control loop 50 having a relatively low sensitivity, but relatively high dynamic range, for coarsely cancelling the outside magnetic field $B_{OUT}$ (e.g., low-frequency cancellation of the outside magnetic field $B_{OUT}$ contributed by the Earth's magnetic field (e.g., any of the techniques described in U.S. application Ser. No. 16/752,393, entitled "Neural Feedback Loop Filters for Enhanced Dynamic Range Magnetoencephalography (MEG) Systems and Methods," which is expressly incorporated herein by reference, a broadband cancellation technique, and/or the harmonic frequency band cancellation techniques described in U.S. Provisional Application Ser. No. 62/975,693, entitled "Nested and Parallel Feedback Control Loops For Ultra-Fine Measurements of Magnetic Fields From the Brain Using a Wearable MEG System", which is expressly incorporated herein by reference), such that the spatial components of the total residual magnetic field $B_{TOT}$ at the fine magnetometers 26b drop to a baseline level within the operating range of the fine magnetometers 26b, and subsequently employing a fine feedback control loop 52 having a relatively high sensitivity, but a low dynamic range that encompasses this baseline level for finely cancelling the outside magnetic field $B_{OUT}$ (e.g., low-frequency cancellation of the outside magnetic field $B_{OUT}$ contributed by the Earth's magnetic field, broadband cancellation, and/or the harmonic frequency band cancellation techniques, such that the spatial components of the total residual magnetic field $B_{TOT}$ at the fine magnetometers 26b further drop from the baseline level to an even lower level, and essentially consists of only the spatial components of the MEG magnetic field $B_{MEG}$. The signal acquisition unit 18 is also configured for managing the coarse feedback control loop 50 and fine feedback control loop 52 by employing a management control loop 54.

In particular, the coarse feedback control loop 50 and fine feedback control loop 52 are implemented in the processor 30, with the coarse feedback control loop 50 coarsely controlling the set of magnetic field actuators 28 in response to input from the coarse magnetometers 26a, and the fine feedback control loop 52 finely controlling the set of magnetic field actuators 28 in response to input from the fine magnetometers 26b. Although the coarse feedback control loop 50 is illustrated as receiving input from three coarse magnetometers 26a, and the fine feedback control loop 52 is illustrated as receiving input from three fine magnetometers 26b, it should be appreciated that the coarse feedback control loop 50 can receive input from more or less coarse magnetometers 26a, including only one coarse magnetometer 26a, and the fine feedback control loop 52 can receive input from more or less fine magnetometers 26b, including only one fine magnetometer 26b. Furthermore, although the coarse feedback control loop 50 and fine feedback control loop 52 are illustrated as receiving input from an equal number of coarse magnetometers 26a and fine magnetometers 26b, the coarse feedback control loop 50 and fine feedback control loop 52 may receive input from an unequal number of coarse magnetometers 26a and fine magnetometers 26b, including a number of coarse magnetometers 26a that is greater or less the number of fine magnetometers 26b.

Initially, due to the relatively low dynamic range of the fine magnetometers 26b, the magnitude of the total residual magnetic field $B_{TOT}$ is too great for the fine magnetometers 26b to detect the total residual magnetic field $B_{TOT}$. However, due to the relatively high dynamic range of the coarse magnetometers 26a, the spatial components of the total residual magnetic field $B_{TOT}$ can be respectively detected by the coarse magnetometers 26a, which outputs coarse error signals $SC_{ERR}$ corresponding to the spatial components of the detected total residual magnetic field $B_{TOT}$.

When the magnitude of the total residual magnetic field $B_{TOT}$ is above the dynamic range of the fine magnetometers 26b, the processor 30 acquires the coarse error signals $SC_{ERR}$ output by the coarse magnetometers 26a in response to detecting the spatial components of the total residual magnetic field $B_{TOT}$, computes the characteristics (namely, the amplitude and phase) of the actuated magnetic field $B_{ACT}$ estimated to minimize the coarse error signals $SC_{ERR}$ output by the coarse magnetometers 26a, and generates a corresponding noise-cancelling control signal C for output to the set of magnetic field actuators 28 for at least partially cancelling the outside magnetic field $B_{OUT}$ at the fine magnetometers 26b, and ultimately suppressing the total residual magnetic field $B_{TOT}$ to a baseline level at the fine magnetometers 26b.

In accordance with the noise-cancelling control signal C output by the processor 30, the set of magnetic field actuators 28 generates the actuated magnetic field $B_{ACT}$, which combines with the outside magnetic field $B_{OUT}$ (along with weak MEG magnetic field $B_{MEG}$ from the brain 14) to create a total residual magnetic field $B_{TOT}$ at the fine magnetometers 26b having spatial components that are at baseline level within the operating range of the fine magnetometers 26b.

Once the spatial components of the total residual magnetic field $B_{TOT}$ are at the baseline level, they can be respectively detected by the fine magnetometers 26b, which outputs fine error signals $SF_{ERR}$ corresponding to the spatial components of the detected total residual magnetic field $B_{TOT}$. The processor 30 then acquires the fine error signals $SF_{ERR}$ output by the fine magnetometers 26b in response to detecting the spatial components of the total residual magnetic field $B_{TOT}$, computes the characteristics of the actuated magnetic field $B_{ACT}$ estimated to minimize the fine error signals $SF_{ERR}$ output by the fine magnetometers 26b, and generates a corresponding noise-cancelling control signal C for output to the set of magnetic field actuators 28 for at least partially cancelling the outside magnetic field $B_{OUT}$ at the fine magnetometers 26b, and ultimately suppressing the total residual magnetic field $B_{TOT}$ to a lower level than the baseline level at the fine magnetometers 26b.

In accordance with the noise-cancelling control signal C output by the processor 30, the set of magnetic field actuators 28 generates the actuated magnetic field $B_{ACT}$, which combines with the outside magnetic field $B_{OUT}$ (along with weak MEG magnetic field $B_{MEG}$ from the brain 14) to create a total residual magnetic field $B_{TOT}$ having spatial components at the fine magnetometers 26b that are at the baseline level. At this point, the fine error signals $SF_{ERR}$ can serve to collect MEG signals $S_{MEG}$ representative of the spatial components of the MEG magnetic field $B_{MEG}$ for further processing by the signal processing unit 20 to identify and localize neural activity in the brain 14 of the user 12.

It should be appreciated that, in the illustrated embodiment, the coarse magnetometers 26a and fine magnetometers 26b are capable of detecting the total residual magnetic field $B_{TOT}$ in three dimensions (x, y, and z), and the set of magnetic field actuators 28 includes three magnetic field actuators 28a-28c (shown in FIG. 2) capable of generating the actuated magnetic field $B_{ACT}$ in three dimensions (x, y, and z). As such, each of the coarse error signals $SC_{ERR}$ and fine error signals $SF_{ERR}$ respectively output by the coarse magnetometers 26a and fine magnetometers 26b to the processor 30, and the control signal C output by the processor 30 to the respective magnetic field actuators 28a-28c, is a vector (i.e., comprises an x-component, y-component, and z-component), such that the outside magnetic field $B_{OUT}$ can be cancelled in three dimensions.

In an alternative embodiment, the signal acquisition unit 18 only employs the coarse feedback control loop 50 for at least partially cancelling the outside magnetic field $B_{OUT}$, such that the spatial components of the total residual magnetic field $B_{TOT}$ at the fine magnetometers 26b drop to a baseline level within the operating range of the fine magnetometers 26b. In this case, the signal acquisition unit 18 does not have a fine feedback control loop 52, and the processor 30 only uses the coarse error signals $SC_{ERR}$ output by the coarse magnetometers 26a to compute the characteristics of the actuated magnetic field $B_{ACT}$ estimated to suppress the total residual magnetic field $B_{TOT}$ to near-zero at the fine magnetometers 26b, even after the spatial components of the total residual magnetic field $B_{TOT}$ at the fine magnetometers 26b are already at the baseline level, such that the fine magnetometers 26b remain in an operating range.

Whether the signal acquisition unit 18 employs both the coarse feedback control loop 50 and the fine feedback control loop 52 to cancel the outside magnetic field $B_{OUT}$, or employs only the coarse feedback control loop 50 to cancel the outside magnetic field $B_{OUT}$, it can be appreciated that the signal acquisition unit 18 is capable of coarsely cancelling a large portion of the outside magnetic field $B_{OUT}$, while still collecting signals from the fine magnetometers 26b sensitive enough to measure the weaker MEG magnetic field $B_{MEG}$ generated by the neural activity in the brain 14 of the user 12.

The processor 30 employs the management control loop 54 to manage how the coarse feedback control loop 50 and fine feedback control loop 52 are employed (e.g., how the coarse error signals $SC_{ERR}$ output by the coarse magnetometers 26a and the fine error signals $SF_{ERR}$ output by the fine magnetometers 26b are to be used) for optimal cancellation of the outside magnetic field $B_{OUT}$, and thus optimal suppression of the total residual magnetic field $B_{TOT}$, and corrects additional factors that can change more slowly over time, such as, e.g., calibrating the magnetometers 26 (e.g., using calibration techniques described in U.S. Provisional Application Ser. No. 62/975,709, entitled "Self-Calibration of Flux Gate Offset and Gain Drift To Improve Measurement Accuracy Of Magnetic Fields From the Brain Using a Wearable MEG System", which is expressly incorporated herein by reference), and optimizing performance metrics in the signal acquisition unit 18, either globally or locally (e.g., using optimal control methods disclosed in U.S. Provisional Application Ser. No. 62/975,727, entitled "Optimal Methods to Feedback Control and Estimate Magnetic Fields to Enable a Wearable MEG System to Measure Magnetic Fields from the Brain", which is expressly incorporated herein by reference), adapting to changing time delays in computations, etc.

The management control loop 54 manages the coarse feedback control loop 50 and fine feedback control loop 52 based on whether the fine magnetometers 26b are in-range or out-of-range, e.g., by considering coarse error signals $SC_{ERR}$ from the coarse magnetometers 26a and ignoring fine error signals $SF_{ERR}$ if the fine magnetometers 26b are out-of-range, and ignoring coarse error signals $SC_{ERR}$ from the coarse magnetometers 26a and considering fine error signals $SC_{ERR}$ from the fine magnetometers 26b if the fine magnetometers 26 are in-range. The management control loop 54 may monitor the spatial component of the total residual magnetic field $B_{TOT}$ and the overall behavior and history of the signal at each fine magnetometer 26b to determine whether or not the fine magnetometer 26b is in-range or out-of-range. It is noted that the spatial components of the total residual magnetic field $B_{TOT}$ at the fine magnetometers 26b may be substantially different from each other, and thus, some of the fine magnetometers 26b may be in-range, while other fine magnetometers 26b may be out-of-range.

With knowledge of whether each of the fine magnetometers 26b are in-range or out-of-range, the management control loop 54 may generally activate the fine feedback control loop 52 after initiating activation of the coarse feedback control loop 50. In this manner, as discussed above, the coarse feedback control loop 50 may coarsely control the actuated magnetic field $B_{ACT}$ in a manner that at least partially cancels the outside magnetic field $B_{OUT}$, and thus suppresses the total residual magnetic field $B_{TOT}$ at the fine magnetometers 26b to a baseline level, such that the at least one of magnetometers 26b comes in-range. The management control loop 54 may then activate the feedback control loop 52 to finely control the actuated magnetic field $B_{ACT}$ in a manner that further suppresses the total residual magnetic field $B_{TOT}$ at the fine magnetometer(s) 26b that just came in-range to a lower level.

In one embodiment, the management control loop 54 strictly activates only the coarse feedback control loop 50 (e.g., if one of the fine magnetometers 26b is out-of-range) or only the fine feedback control loop (e.g., if all of the fine magnetometers 26 are in-range), but not both the coarse feedback control loop 50 and the fine feedback control loop 52 at the same time. In this case, the management control loop 54 will only consider coarse error signals $SC_{ERR}$ from the coarse magnetometers 26a when the coarse feedback control loop 50 is active, and will only consider fine error signals $SF_{ERR}$ from the fine magnetometers 26b when the fine feedback control loop 52 is active.

In another particularly preferred embodiment, however, the management control loop 54, at any given time, may not strictly activate only the coarse feedback control loop 50 or strictly activate only the fine feedback control loop 52, and thus, both of the coarse feedback control loop 50 and fine feedback control loop 52 may be at least partially activated. The management control loop 54 may choose to consider only the fine error signals $SF_{ERR}$ from the fine magnetometers 26b that are in-range. In this case, the management control loop 54 may determine whether or not the fine magnetometer 26b is in-range, and performs a "sensor hand-off" procedure, and in particular, switches back and forth between consideration of a coarse error signal $SC_{ERR}$ from any given coarse magnetometer 26a and consideration of a fine error signal $SF_{ERR}$ from any given fine magnetometer 26b. It is understood that only some of the fine magnetometers 26b may be out-of-range at any given moment, so the sensor hand-off procedure can be from one, some, or all coarse magnetometers 26a to one, some, or all of the fine magnetometers 26b.

For example, if the management control loop 54 is currently considering a coarse error signal $SC_{ERR}$ from a coarse magnetometer 26, and a previously unavailable fine magnetometer 26b is deemed to be in-range, the processor 30 may then ignore a coarse error signal $SC_{ERR}$ from at least one coarse magnetometer 26a that is in proximity to the previously unavailable fine magnetometer 26b, and instead consider the more accurate fine error signal $SF_{ERR}$ from this previously unavailable fine magnetometer 26b (in essence, passing or handing off detection of the total residual magnetic field $B_{TOT}$ from the coarse magnetometer(s) 26b to the fine magnetometer 26b).

On the contrary, if the management control loop 54 is currently considering a fine error signal $SF_{ERR}$ from a fine magnetometer 26b, and the fine magnetometer 26b is subsequently deemed to fall out-of-range for any one of a variety of reasons (e.g., if the user 12, and thus the fine magnetometer 26b, gets too close to a power outlet, a fridge magnet, a cell phone, or perhaps if the user 12 turns their head so suddenly that the total residual magnetic field $B_{TOT}$ to which the fine magnetometer 26b varies too quickly), the management control loop 54 may then ignore the fine error signal $SF_{ERR}$ from that fine magnetometer 26b, and instead consider the coarse error signal $SC_{ERR}$ from at least one coarse magnetometer 26a in proximity to the now unavailable fine magnetometer 26b (in essence, passing or handing off detection of the total residual magnetic field $B_{TOT}$ from the fine magnetometer 26b to the coarse magnetometer 26a).

Thus, in this manner, the management control loop 54 may operate the fine feedback control loop 52 to control the actuated magnetic field $B_{ACT}$ based on the fine error signals $SF_{ERR}$ respectively output by fine magnetometers 26b as they come in-range. The management control loop 54 may operate the fine feedback control loop 52 to prevent control of the actuated magnetic field $B_{ACT}$ based on the fine error signals $SF_{ERR}$ respectively output by fine magnetometers 26b as they go out-of-range.

In an optional embodiment, the management control loop 54 may weight the fine magnetometers 26b, in which case, the management control loop 54 may not perform a "sensor hand-off" procedure, per se, but may assign a weight a to any given fine magnetometer 26b between a value 0 (no weight) and 1 (full weight). For example, the management control loop 54 may monitor different operating parameters of a fine magnetometer 26b to determine whether the fine magnetometer 26b is in a linear operating range, or outside of the linear operating range, but not saturated (non-linear operating range), or is saturated. If the fine magnetometer 26b is found to be in the linear operating range, the weighting a assigned to the fine magnetometer 26b can be 1 (i.e., full weight); if the fine magnetometer 26b is found to be saturated, the weighting a assigned to the fine magnetometer 26b can be 0 (i.e., no weight); and if the fine magnetometer 26b is found to be in the non-linear operating range, the weighting a assigned to the fine magnetometer 26b can be between 0 and 1 (i.e., partial weight), depending on how close the fine magnetometer 26b is to saturation.

As discussed above, the management control loop 54 is configured for correcting factors that can change more slowly over time to optimize the cancellation of the outside magnetic field $B_{OUT}$. For example, the management control loop 54 may be configured for implementing adaptions to slow changes of the coarse feedback control loop 50 and fine feedback control loop 52 over time. The management control loop 54 is configured for identifying and determining parameters and coefficients of the signal acquisition unit 18 and the outside magnetic field $B_{OUT}$. The management control loop 54 is configured for employing computational algorithms to determine unknown parameters from the coarse error signals $SC_{ERR}$ and fine error signals $SF_{ERR}$ output by the coarse magnetometers 26a and fine magnetometers 26b, such as fitting of physical and calibrated mathematical and numerical models to the coarse error signals $SC_{ERR}$ and fine error signals $SF_{ERR}$ to identify missing or insufficiently known coefficients and parameters. Such parameters and coefficients can include offset and gain coefficients for the coarse magnetometers 26a, gain constants for the fine magnetometers 26b, actuator gains and offsets for the set of magnetic field actuators 28, electronics time delay latency coefficients in the coarse feedback control loop 50 and fine feedback control loop 52 (i.e., the amount of time between generating the coarse error signal $SC_{ERR}$ or fine error signal $SF_{ERR}$ and activating the set of magnetic field actuators 28), and other parameters of the signal acquisition unit 18. The management control loop 54 may determine coefficients and parameters for different temporal and spatial ranges. Likewise, the gain that the set of magnetic field actuators 28 may have on the coarse magnetometers 26a and fine magnetometers 26b may differ with the placement and location offset of magnetic field actuators 28 (e.g., as the head of the user 12 moves or the support structure 24 deforms). The management control loop 54 may identify at least one, some, or all of the coefficients or parameters over these changing conditions.

In one exemplary instance, a mathematical and numerical model of the signal acquisition unit 18, or a portion thereof, has some coefficients or parameters that are considered poorly or insufficiently known. In another exemplary instance, a mathematical and numerical model of the signal acquisition unit 18 does not have a predetermined structure, and the coefficients or parameters consist of transfer functions or linear mappings from one set of signals to another. The management control loop 54 may compare the response of a structured or unstructured model of the signal acquisition unit 18 to the measurements from the coarse magnetometers 26a and fine magnetometers 26b, and the coefficients or parameters may be varied until any disagreement between the mathematical model of the signal acquisition unit 18 and the actual measured signals is decreased. The coefficients or parameters of the mathematical model that achieve such a decrease in disagreement are the estimated parameters of the signal acquisition unit 18 (meaning, if the mathematical model with selected parameter values x, y, and z best matches the actual measured behavior of the system, then the values x, y, and z are a system identification estimate of the poorly or insufficiently known coefficients or parameters of the system). In determining the coefficients or parameters of the signal acquisition unit 18, the management control loop 54 may employ weighted least squares, observer filters, Kalman filters, Wiener filters, or other filters. The management control loop 54 may employ time domain, frequency domain, recursive techniques, parametric and non-parametric methods, linear and nonlinear optimization techniques including gradient descent, matrix methods, convex methods, non-convex methods, neural networks, genetic algorithms, fuzzy logic, and machine learning methods.

The management control loop 54 may perform calibration techniques prior to operating the neural activity measurement system 10, or calibration techniques may be performed in real-time as the neural activity measurement system 10 operates. For example, prior to usage, the signal acquisition unit 18 may be calibrated by applying a known magnetic field in a controlled shielded setting (e.g., to characterize the coarse magnetometers 26a for their offsets and gain measurements). However, the properties of coarse magnetometers 26a, fine magnetometers 26b, or set of magnetic field actuators 28 may vary due to environmental variations, such as, e.g., variations in temperature, laser power (for magnetometers that utilize lasers), motion or deformation of the support structure 24, or other deformations, such as bending of the coarse magnetometers 26a, fine magnetometers 26b, or offset of magnetic field actuators 28 due to temperature or mechanical stresses. Thus, in addition to performing calibrations ahead of time, the management control loop 54 may perform calibrations techniques during system operation. For example, if the offsets and gains of the coarse magnetometers 26a change during usage of the neural activity measurement system 10, the management control loop 54 may estimate the offsets and gains of the coarse magnetometers 26a in real time (i.e., as the neural activity measurement system 10 is running), e.g., by estimating and comparing the offset of one coarse magnetometer against the measurements of other coarse or fine magnetometers. Further details discussing the calibration of coarse magnetometers are disclosed in U.S. Provisional Application Ser. No. 62/975,709, entitled "Self-Calibration of Flux Gate Offset and Gain Drift To Improve Measurement Accuracy Of Magnetic Fields From the Brain Using a Wearable MEG System", which is expressly incorporated herein by reference.

It should be appreciated that, in the case where the signal acquisition unit 18 comprises multiple sets of magnetic field actuators 28 and processors 30, the components, along with the coarse feedback control loop 50, fine feedback control loop 52, and management control loop 54, illustrated in FIG. 4 may be duplicated. In this case, a subset of the coarse magnetometers 26a will be associated with each coarse feedback control loop 50, and a subset of the fine magnetometers 26b will be associated with each fine feedback control loop 52. Because the actuated magnetic field $B_{ACT}$ generated by each set of the magnetic field actuators 28 will affect all of the coarse magnetometers 26a and all of the fine magnetometers 26b, the processors 30 may communicate with each other to generate the proper noise-cancelling control signals C that will result in the composite cancelling magnetic field $B_{ACT}$ to be generated by the combination of sets of magnetic field actuators 28 to cancel the outside magnetic field $B_{OUT}$. Alternatively, a single processor 30 may be used to control all sets of the magnetic field actuators 26.

One issue that arises with attempting to approximately cancel the outside magnetic field $B_{OUT}$ is that, although the magnetic field actuators 28 are preferably spatially located as close as possible to the fine magnetometers 26a (and, in fact, may be integrated with the fine magnetometers 26b as a single unit), the measurements of the outside magnetic field $B_{OUT}$ are at the locations of the coarse magnetometers 26b, which may be spatially located a significant distance from the magnetic field actuators 28. Therefore, the actuated magnetic field $B_{ACT}$ that cancels the outside magnetic field $B_{OUT}$ at the fine magnetometers 26b, as illustrated in FIG. 3, is experienced by the coarse magnetometers 26b (which are far from the magnetic field actuators 28) much differently than the actuated magnetic field $B_{ACT}$ experienced by the fine magnetometers 26b (which are close to the magnetic field actuators 28). In particular, the coarse magnetometers 26a will be affected by the actuated magnetic field $B_{ACT}$ generated by the magnetic field actuators 28 much less than the fine magnetometers 26b will be affected by the same actuated magnetic field $B_{ACT}$. Furthermore, the outside magnetic field $B_{OUT}$, itself, may spatially vary, and thus, the spatial components of the outside magnetic field $B_{OUT}$ at the coarse magnetometers 26a may substantially differ from the spatial components of the outside magnetic field $B_{OUT}$ at the fine magnetometers 26a.

The outside magnetic field $B_{OUT}$ must be cancelled even though the total residual magnetic field $B_{TOT}$ (i.e., the sum of the outside magnetic field $B_{OUT}$ and the actuated magnetic field $B_{ACT}$) measured by the coarse magnetometers 26b may differ substantially from the total residual magnetic field $B_{TOT}$ present at the fine magnetometers 26a, for the primary reason that the coarse magnetometers 26b are located further away from the magnetic field actuators 28 than the fine magnetometers 26a are located from the magnetic field actuators 28. Thus, because the coarse magnetometers 26a detect the respective spatial components of the total residual magnetic field $B_{TOT}$ remotely from the fine magnetometers 26b, a significant error may potentially be created in the coarse feedback control loop 50 used to coarsely cancel the outside magnetic field $B_{OUT}$ at the fine magnetometers 26b, because the coarse feedback control loop 50 may be falsely reacting to the total residual magnetic field $B_{TOT}$ at the location of the coarse magnetometers 26a rather than the true total residual magnetic field $B_{TOT}$ that occurs at the fine magnetometers 26b, and that must be cancelled to bring them into their operating range.

Thus, without correcting the total residual magnetic field $B_{TOT}$ measured by the at the coarse magnetometers 26a, the coarse feedback loop 50 will be operating with the wrong value of the total residual magnetic field $B_{TOT}$. As a result, substantive inaccuracies in the suppression of the total residual magnetic field $B_{TOT}$ at the fine magnetometers 26b may occur.

Figure 5:
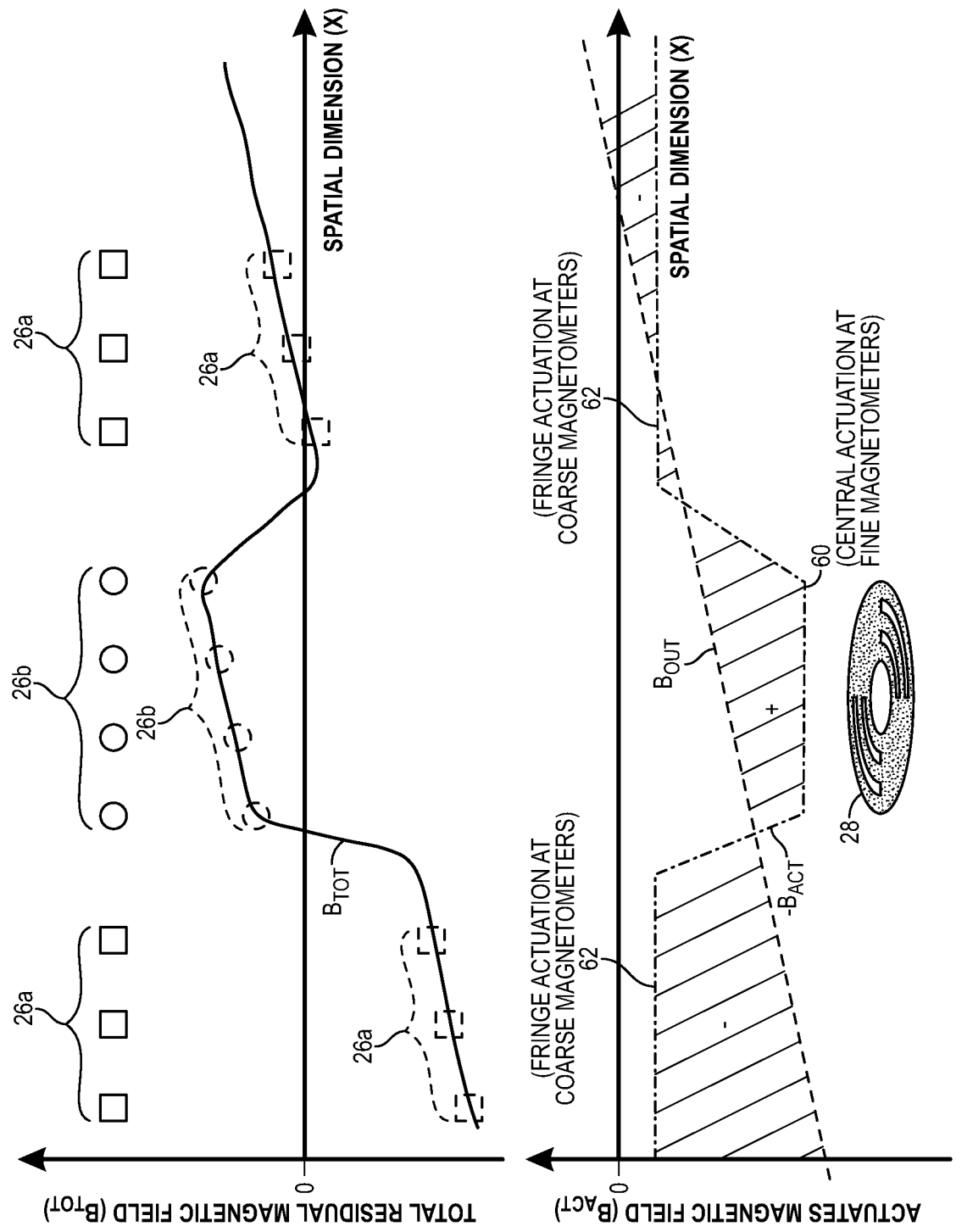
FIG. 5 is a diagram illustrating an exemplary actuated magnetic field generated by the signal acquisition unit of FIG. 4 to illustrate estimation of a total residual magnetic field at the fine magnetometer sensors from available measurements of the total residual magnetic field at the coarse magnetometer sensors.

For example, with reference to FIG. 5, a number of coarse magnetometers 26a (represented as filled squares) and a number of fine magnetometers 26b (represented as filled circles) are located, in this example along a single axis (e.g., along the x-dimension). For purposes of illustration, three coarse magnetometers 26a are shown on the left-side of the x-axis, four fine magnetometers 26b are shown in the center of the x-axis, and three other coarse magnetometers 26a are shown on the right-side of the x-axis. It should be appreciated, however, that any number of coarse magnetometers 26a and any number of fine magnetometers 26b may be arranged relative to each other in any suitable manner, including along other dimensions, namely the y- and z-dimensions.

The course magnetometers 26a and fine magnetometers 26b are exposed to an exemplary outside magnetic field $B_{OUT}$, which for the purposes of brevity and clarity in illustration, comprises only the Earth's magnetic field, although the outside magnetic field $B_{OUT}$ may comprise other types of magnetic noise as discussed above. On the length scale of the signal acquisition unit 18, the outside magnetic field $B_{OUT}$ can be assumed to have certain properties. An appropriate and sufficiently accurate representation of the outside field $B_{OUT}$ might have both a uniform ($0^{th}$ order) spatial component and may also have a linear (first order) spatial component, although it is possible to include additional spatial components, such as $2^{nd}$ order, $3^{rd}$ order, $4^{th}$ order, etc., components, or to choose different basis functions to represent the outside field $B_{OUT}$. Thus, in this example, the outside magnetic field $B_{OUT}$ illustrated in FIG. 5 (bottom panel, dashed line) is the type of outside magnetic field that needs to be cancelled, so that the fine magnetometers 26b can come in-range. In this illustrated case, the outside magnetic field $B_{OUT}$ is negative starting at the left of the magnetometers 26, and becomes less negative to the right, thereby having a positive slope.

A magnetic field actuator 28 is placed directly underneath the four fine magnetometers 26b for generating the cancelling actuated magnetic field $B_{ACT}$ to cancel the outside magnetic field $B_{OUT}$ at the location of the fine magnetometers 26b. An exemplary actuated magnetic field $B_{ACT}$ is shown, which may correspond to one of the initial actuated magnetic field $B_{ACT}$ applied by the magnetic field actuator 28 and which has not yet achieved complete cancellation of the outside magnetic field $B_{OUT}$ at the locations of the fine magnetometers 26b. It should be appreciated that in order to compare the top and bottom panels of FIG. 5, it is convenient to show minus of the actuated magnetic field ($-B_{ACT}$) in the bottom panel of FIG. 5.

The present intent is to illustrate how the total residual magnetic field $B_{TOT}$ at the fine magnetometers 26b substantially differs from the total residual magnetic field $B_{TOT}$ at the coarse magnetometers 26b due to the significant differences in distance between the fine magnetometers 26b and the coarse magnetometers 26a from the magnetic field actuator 28. The actuated magnetic field $B_{ACT}$, which in this exemplary instance, has a relatively strong central actuating portion 60 at the fine magnetometers 26b, and less strong (or fringe) actuating portions 62 at the coarse magnetometers 26a. Ignoring any minor contribution by the MEG magnetic field $B_{MEG}$ (which is essentially zero at the coarse magnetometers 26a) for purposes of brevity, the total residual magnetic field $B_{TOT}$ is the summation of the outside magnetic field $B_{OUT}$ and the actuated magnetic field $B_{ACT}$. This summation is shown at the top of FIG. 5, and has a tilted-hat shape due to the positive slope of the outside magnetic field $B_{OUT}$ plus the hat shape (strong central actuating portions 60 plus weak fringe actuating portions 62) of the actuated field $B_{ACT}$.

In this exemplary instance, the measurements taken by the coarse magnetometers 26a are available to the coarse feedback control loop 50 of the processor 30, while the measurements from the fine magnetometers 26b are not yet available, because the total residual magnetic field $B_{TOT}$ has not yet been cancelled sufficiently to bring the fine magnetometers 26b in-range. Thus, as discussed above, available measurements of the total residual magnetic field $B_{TOT}$ at the coarse magnetometers 26a are used by the coarse control feedback loop 50 to estimate the total residual magnetic field $B_{TOT}$ at the fine magnetometers 26b, and the characteristics of the actuated magnetic field $B_{ACT}$ are then selected by the coarse control feedback loop 50 based on this estimate.

In the embodiment illustrated in FIG. 3, the set of magnetic field actuators 28 are spatially much closer to the fine magnetometers 26b (and, in fact, may be integrated with the fine magnetometers 26b as a single unit) than the coarse magnetometers 26a. Thus, despite the fact that the coarse magnetometers 26a and fine magnetometers 26b may essentially experience the same outside magnetic field $B_{OUT}$, due to the spatial differences between coarse magnetometers 26a and fine magnetometers 26b relative to the proximate magnetic field actuators 28, the coarse magnetometers 26a will be affected by the actuated magnetic field $B_{ACT}$ generated by the magnetic field actuators 28 much less than the fine magnetometers 26b will be affected by the same actuated magnetic field $B_{ACT}$ (e.g., 20%).

Thus, it follows that the measurements of the total residual magnetic field $B_{TOT}$ at the coarse magnetometers 26a may be quite different than the true (not yet measured) total residual magnetic field $B_{TOT}$ at the fine magnetometers 26b. Ignoring the minute contribution of the MEG magnetic field $B_{MEG}$ for purposes of simplicity, the coarse magnetometers 26a and fine magnetometers 26b will measure a different total residual magnetic field $B_{TOT}=B_{OUT}+B_{ACT}$, because even though the outside magnetic field $B_{OUT}$ may be the same at both coarse magnetometers 26a and fine magnetometers 26b, the actuated magnetic field $B_{ACT}$ will differ between the coarse magnetometers 26a and fine magnetometers 26b based on their different proximities to the magnetic field actuators 28.

Indeed, in the exemplary case illustrated in FIG. 5, the total residual magnetic field $B_{TOT}$ at the coarse magnetometers 26a is strongly negative on the left, and is modestly positive on the right, while the true unmeasured total residual magnetic field $B_{TOT}$ at the fine magnetometers 26b is strongly positive in this example, and this is because these fine magnetometers 26b experience a much stronger central actuating portion 60 of the actuated magnetic field $B_{ACT}$ from the magnetic field actuator 28 than do the far-away coarse magnetometers 26a that only experience the fringe actuating portions 62 of the actuated magnetic field $B_{ACT}$ from the magnetic field actuator 28.

Thus, absent estimation of the spatial components of the total residual magnetic field $B_{TOT}$ respectively at each fine magnetometer 26b, cancellation of the outside magnetic field $B_{OUT}$ based directly (i.e., without correction) on the coarse error signals $SC_{ERR}$ output by the coarse magnetometers 26a in FIG. 5 may be insufficient to cancel the outside magnetic field $B_{OUT}$ occurring at the fine magnetometers 26b.

Significantly, as will be described in further detail below, the estimation method implemented on processor 30 is configured for compensating for the difference between the measurements of the total residual magnetic field $B_{TOT}$ at the coarse magnetometers 26a and the true total residual magnetic field $B_{TOT}$ at the fine magnetometers 26b when attempting to cancel the outside magnetic field $B_{OUT}$ occurring at the fine magnetometers 26b. The processor 30 accomplishes this by inferring the total residual magnetic field $B_{TOT}$ at the fine magnetometers 26b from the available measurements of the total residual magnetic field $B_{TOT}$ taken by the coarse magnetometers 26a. Then, based on the inferred total residual magnetic field $B_{TOT}$ at the fine magnetometers locations 26b, the coarse feedback loop 50 determines the characteristics of the actuated magnetic field $B_{ACT}$ required to drive the total residual magnetic field $B_{TOT}$ at the fine magnetometers 26b to near-zero (i.e., a baseline level at which the fine magnetometers 26b are now in-range). The processor 30 may achieve this even if, as exemplified in FIG. 5, the total residual magnetic field $B_{TOT}$ at the coarse magnetometers 26a is substantially different (e.g. is negative on the left, and close to zero and slightly positive on the right) from the total residual magnetic field $B_{TOT}$ at the fine magnetometers 26b (e.g. is substantially positive), which is due to the central actuating portion 60 of the actuated magnetic field $B_{ACT}$ at the fine magnetometers 26b relative to the fringe actuating portions 62 of the actuated magnetic field $B_{ACT}$ at the coarse magnetometers 26a.

To further illustrate this, in one exemplary situation, there may be one coarse magnetometer 26a at one location, one fine magnetometer 26b at another location, and one actuating coil 28 close to the location of the fine magnetometer 26b. It should be appreciated that this exemplary situation has been simplified for illustration purposes only, and that the invention applies more broadly to many coarse magnetometers 26a and fine magnetometers 26b, and more than one magnetic field actuator 28. Assume for purposes of illustration only that the outside magnetic field $B_{OUT}$ is constant in space and has a value of 52 microTesla (52 uT). To attempt to cancel this outside magnetic field $B_{OUT}$ to bring the fine magnetometer 26b into its operating range, suppose the magnetic field actuator 28 is currently applying an actuated magnetic field $B_{ACT}$ of minus 50 microTesla (−50 uT).

Suppose that the magnetic field actuator 28 immediately adjacent to the fine magnetometer 26b (where a direct measurement is not yet available), but is far from the coarse magnetometer 26a (where a measurement is available). Thus, assuming that 100% of the strength of the actuated magnetic field $B_{ACT}$ reaches the nearby fine magnetometer 26b (i.e., the actuated magnetic field $B_{ACT}$ at the fine magnetometer 26b is minus 50 microTesla (−50 uT)), but only 20% of the strength of the actuated magnetic field $B_{ACT}$ reaches the further away coarse magnetometer 26a (i.e., the actuated magnetic field $B_{ACT}$ at the fine magnetometer 26b is minus 10 microTesla (−10 uT), the total residual magnetic field $B_{TOT}$ at the coarse magnetometer 26a will be $B_{TOT}$=52 uT+20%×(−50 uT)=52 uT−10 uT=42 uT. In contrast, the true total residual magnetic field $B_{TOT}$ at the coarse magnetometer 26a $B_{TOT}$=52 uT+100%×(−50 uT)=52 uT−50 uT=2 uT.

Evidently, the not-measured total residual magnetic field $B_{TOT}$ at the fine magnetometer 26b (2 uT) is very different than the total residual magnetic field $B_{TOT-MEAS}$ measured at by the coarse magnetometer 26a (42 uT). However, the coarse feedback control loop 50 needs to drive the true total residual magnetic field $B_{TOT}$ at the location of the fine magnetometer 26b to near-zero (so that the fine magnetometer 26b can come into range), and it must do so by using information from the total residual magnetic field $B_{TOT-MEAS}$ measured by the coarse magnetometer 26a (42 uT), which is very different. However, the strength of the previously applied actuated magnetic field $B_{ACT}$ is known by the processor 30, since it was generated by the signal acquisition unit 18, itself. Using these two pieces of information; i.e., the present measurement of the total residual magnetic field $B_{TOT-MEAS}$ by the coarse magnetometer 26a (42 uT) and the strength of the previously applied actuated magnetic field $B_{ACT}$ (−50 uT), the processor 30 may accurately infer an estimate of the total residual magnetic field $B_{TOT-EST}$ at the location of the fine magnetometer 26b, while it is still out-of-range.

Specifically, for this simple exemplary case, the estimate of the total residual magnetic field $B_{TOT-EST}$ at the location of the fine magnetometer 26b can be computed as: $B_{TOT-EST}$=$B_{OUT}$+100%×($B_{ACT}$)=$B_{TOT-MEAS}$−20%×($B_{ACT}$)+100%×($B_{ACT}$)=$B_{TOT-MEAS}$+80%×($B_{ACT}$)=42 uT+80%×(−50 uT)=2 uT. The result is an accurate estimate of the true and unmeasured total residual magnetic field $B_{TOT-EST}$ at the location of the out-of-range fine magnetometer 26b (2 uT) based on the available current measurement of the total residual magnetic field $B_{TOT-MEAS}$ at the coarse magnetometer 26a (42 uT) and on the knowledge of the strength of actuated magnetic field $B_{ACT}$ (−50 uT) at the previous time step. This accurate estimate of the total residual magnetic field $B_{TOT-EST}$ at the location of the fine magnetometer 26b can now be provided to the control feedback control loop 50 at the current time step, so that the coarse feedback control loop 50 can continue to drive the true total residual magnetic field $B_{TOT}$ at the location of the fine magnetometer 26b to near-zero, so that the fine magnetometer 26b can be brought into range.

It should be appreciated that, although the total residual magnetic field estimate $B_{TOT-EST}$ at the fine magnetometer 26b has been illustrated as being inferred from the total residual magnetic field measurement $B_{TOT-MEAS}$ at the coarse magnetometer 26a for purposes of simplicity, in practice, the total residual magnetic field estimate $B_{TOT-EST}$ at the fine magnetometer 26b will typically be inferred from the total residual magnetic field measurements $B_{TOT-MEAS}$ at multiple coarse magnetometers 26a and any other fine magnetometers 26b that are in-range, as discussed in further detail below. It should be understood that the outside magnetic field $B_{OUT}$ and actuated magnetic field $B_{ACT}$ (and thus, the true total residual magnetic field $B_{TOT}$) will differ at the multiple magnetometers 26 from which the total residual magnetic field estimate $B_{TOT-EST}$ at the fine magnetometer 26b will be estimated. The process can be repeated for inferring the total residual magnetic field estimate $B_{TOT-EST}$ at additional fine magnetometers 26b.

In one embodiment, even after the total residual magnetic field $B_{TOT}$ at the fine magnetometers 26b has been driven to the baseline level that allows measurements of the total residual magnetic field $B_{TOT}$ to be actively acquired by the fine magnetometers 26b, the fine feedback control loop 52 of the processor 30 may be configured for correcting or refining the fine error signals $SF_{ERR}$ by continuing to infer the total residual magnetic field $B_{TOT}$ at the fine magnetometers 26b not only from the measurements of the total residual magnetic field $B_{TOT-MEAS}$ acquired from the coarse magnetometers 26a, but also from measurements of the total residual magnetic field $B_{TOT-MEAS}$ acquired from the fine magnetometers 26b.

Figure 6:
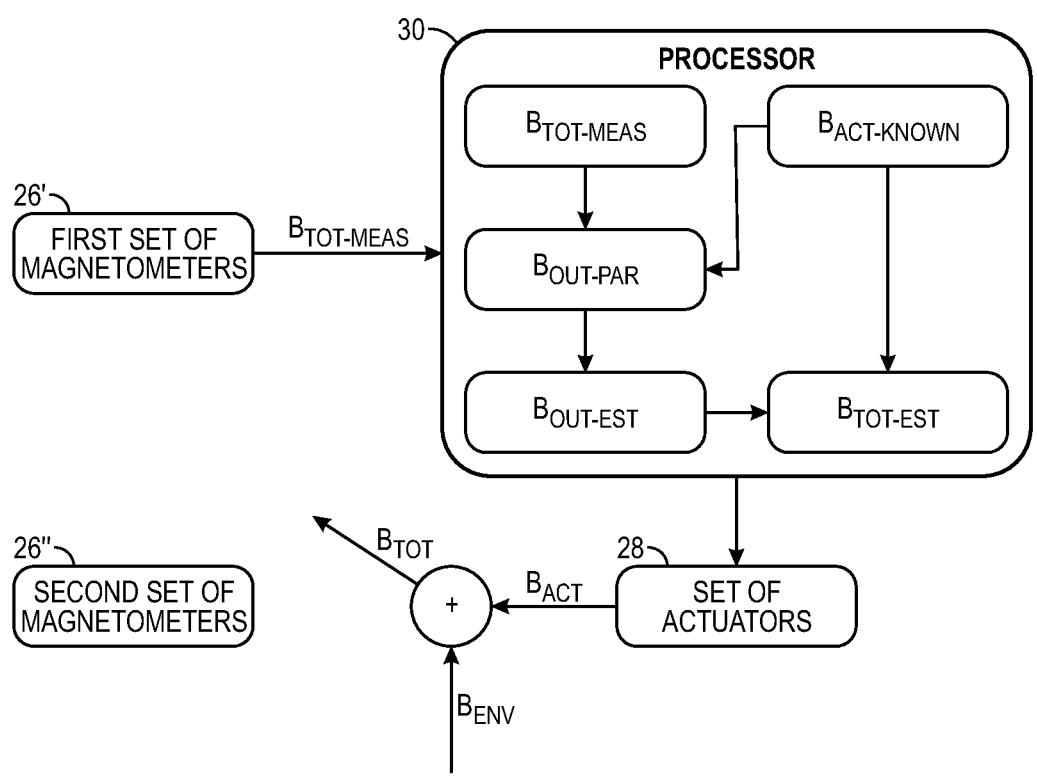
FIG. 6 a block diagram illustrating the estimation of a total residual magnetic field at a second set of magnetometers by a processor of the signal acquisition unit of FIG. 4 based on measurements of the total residual magnetic field at a first set of magnetometers.

Thus, referring now to FIG. 6, the estimation technique employed by the processor 30 may be generalized to infer estimates of the total residual magnetic field $B_{TOT-EST}$ at a first set of magnetometers 26' (comprising coarse magnetometers 26a and/or fine magnetometers 26b) based on measurements of the total residual magnetic field $B_{TOT-MEAS}$ (i.e., the coarse error signals $SC_{ERR}$ and/or fine error signals $SF_{ERR}$) acquired from a second set of magnetometers 26" (comprising coarse magnetometers 26a and/or fine magnetometers 26b).

In an exemplary scenario, the first set of magnetometers 26' from which the measurements of the actual magnetic field $B_{TOT-MEAS}$ are taken comprises only coarse magnetometers 26a prior to the fine magnetometers 26b coming in-range, but may include measurements from the fine magnetometers 26b as they come in-range. The second set of magnetometers 26" at which the total residual magnetic field estimates $B_{TOT-EST}$ are inferred will generally be fine magnetometers 26b that are out-of-range (i.e., at start-up of the signal processing unit 18, such that the fine magnetometers 26b are coming in-range, or when the fine magnetometers 26b have gone out-of-range due to large dynamic variations in the outside magnetic field $B_{OUT}$ from, e.g., an unforeseen spike in the outside magnetic field $B_{OUT}$ like a power surface or the user 12 bring the signal processing unit 18 temporarily near a wall socket or perhaps turning their head too quickly), such that cancellation of the outside magnetic field $B_{OUT}$ may be accurately performed.

However, in another exemplary scenario, the second set of magnetometers 26" at which the total residual magnetic field estimates $B_{TOT-EST}$ are inferred may include fine magnetometers 26b that are in-range (and fully functional), as well as coarse magnetometers 26a, and thus from which measurements of the total residual magnetic fields $B_{TOT-MEAS}$ have been previously taken, such that such measurements taken from the coarse magnetometers 26a and fine magnetometers 26b may be corrected.

Significantly, the inference of the total residual magnetic field estimate $B_{TOT-EST}$ at any given magnetometer 26 from measurements of the total residual magnetic field $B_{TOT-MEAS}$ at multiple other different magnetometers 26 (measurements from both coarse magnetometers 26a and fine magnetometers 26b) can be more accurate than the measurement of the total residual magnetic field $B_{TOT-MEAS}$ at that magnetometer 26, because measurements from many magnetometers 26 provides a more accurate averaged reading that may exceed the accuracy of any one magnetometer 26, even at its own location. Thus, it should be appreciated more broadly that inferring the total residual magnetic field estimate $B_{TOT-EST}$ at a coarse magnetometer 26a or a fine magnetometer 26b that is in-range may still be beneficial. As such, it is possible for the first set of magnetometers 26' and the second set of magnetometers 26" to both include coarse magnetometers 26a and fine magnetometers 26b, and in fact, may both include all of the coarse magnetometers 26a and all of the fine magnetometers 26b that are in-range.

In one embodiment, the processor 30 is configured for initially including the coarse magnetometers 26a in the first set of magnetometers 26', excluding the fine magnetometers 26b from the first set of magnetometers 26', and initially including the fine magnetometers 26b in the second set of magnetometers 26", such that control of the actuated magnetic field $B_{ACT}$ at least partially based on the total residual magnetic field estimates $B_{TOT-EST}$ at the second set of magnetometers 26" suppresses the total residual magnetic field $B_{TOT}$ at the second set of magnetometers 26" to a baseline level, such that the at least one fine magnetometer 26b comes in-range.

The processor 30 may be configured for acquiring the total residual magnetic field measurements $B_{TOT-MEAS}$ from the fine magnetometers 26b, and controlling the actuated magnetic field $B_{ACT}$ is controlled at least partially based on the total residual magnetic field measurements $B_{TOT-MEAS}$ acquired from the fine magnetometers 26b, such that the total residual magnetic field $B_{TOT}$ at the fine magnetometers 26b is suppressed to a lower level. Alternatively, the processor 30 is configured for subsequently including the fine magnetometers 26b in the first set of magnetometers 26', such that control of the actuated magnetic field $B_{ACT}$ at least partially based on the total residual magnetic field estimates $B_{TOT-EST}$ at the second set of magnetometers 26" further suppresses the total residual magnetic field $B_{TOT}$ at the second set of magnetometers 26b to a lower level.

In an alternative embodiment, the processor 30 is configured for including both the coarse magnetometers 26a and the fine magnetometers 26b in the first set of magnetometers 26', determining whether each of the fine magnetometers 26b is in-range (e.g., in a linear operating range or a non-linear operating range) or out-of-range (e.g., saturated), and assigning a weighting to each fine magnetometer 26b based on the in-range or out-of-range determination in a manner such that the control of the actuated magnetic field $B_{ACT}$ at least partially based on the total residual magnetic field estimates $B_{TOT-EST}$ at the second set of magnetometers 26b suppresses the total residual magnetic field $B_{TOT}$ at the second set of magnetometers 26b. For example, the processor 30 may initially assign a relatively low weighting (even a weighting of 0) to any fine magnetometer 26b that is out-of-range, and as each fine magnetometer 26b comes in-range, assign a relatively high weighting to each in-range magnetometer 26b.

The processor 30 is configured for inferring the total residual magnetic field estimates $B_{TOT-EST}$ at the second set of the magnetometers 26" by (1) acquiring the measurements of the total residual magnetic field $B_{TOT-MEAS}$ from the first set of magnetometers 26' (i.e., the coarse error signals $SC_{ERR}$ and/or fine error signals $SF_{ERR}$); (2) determining the known actuated magnetic field $B_{ACT-KNOWN}$ at the magnetometers 26 based on a known profile of the set of magnetic field actuators 28 and the actuation strengths of the magnetic field actuators 28; (3) generating a generic model of the outside magnetic field $B_{OUT-MOD}$ in the vicinity of the magnetometers 26; (4) parameterizing the generic outside magnetic field model $B_{OUT-MOD}$ based on the total residual magnetic field $B_{TOT-MEAS}$ measured by the first set of magnetometers 26' and the known actuated magnetic field $B_{ACT-KNOWN}$ at the first set of magnetometers 26' to generate a parameterized outside magnetic field model $B_{OUT-PAR}$ (representative of the true outside magnetic field model $B_{OUT}$ in the vicinity of the magnetometers 26); (6) determining the outside magnetic field estimates $B_{OUT-EST}$ at the second set of magnetometers 26" based on the parameterized outside magnetic field model $B_{OUT-PAR}$; and (7) determining the total residual magnetic field estimates $B_{TOT-EST}$ at the second set of magnetometers 26" based on the known actuated magnetic field $B_{ACT-KNOWN}$ at the second set of magnetometers 26" and the outside magnetic field estimates $B_{OUT-EST}$ at the second set of magnetometers 26".

In the manner described above, the processor 30 can then use the total residual magnetic field estimates $B_{TOT-EST}$ at the second set of magnetometers 26" to compute the characteristics of the actuated magnetic field $B_{ACT}$ estimated to coarsely and/or finely cancel the outside magnetic field $B_{OUT}$ via the coarse feedback control loop 50 and/or a fine feedback control loop 52 (see FIG. 4), such that the total residual magnetic field $B_{TOT}$ drops to or remains at a level in the operating range of the second set of magnetometers 26", and generates a corresponding noise-cancelling control signal C for output to the set of magnetic field actuators 28.

With regard to acquiring the total residual magnetic field measurements $B_{TOT-MEAS}$ from the first set of magnetometers 26', in an exemplary embodiment, an N' number of magnetometers 26' respectively at an N' number of locations may collect an N'×K coarse measurements of the total residual magnetic field $B_{TOT-MEAS}$ over time in accordance with the discretized matrix:

$$B_{TOT-MEAS} = \begin{bmatrix} B_{TOT-MEAS_{11}} & \cdots & B_{TOT-MEAS_{1K}} \\ \vdots & \ddots & \vdots \\ B_{TOT-MEAS_{N1}} & \cdots & B_{TOT-MEAS_{NK}} \end{bmatrix}. \quad [1]$$

Assuming that the set of magnetometers 26' are vector magnetometers for respectively measuring the x-, y-, and z-components of the total residual magnetic field measurements $B_{TOT-MEAS}$, equation [1] can be expressed as a vector $\vec{B}_{TOT-MEAS}(x, y, z, t)$ that varies over space and time, where x, y, z are the three cardinal directions, and t is time that varies over space and time.

The total residual magnetic field measurements $\vec{B}_{TOT-MEAS}(x, y, z, t)$ at the locations of an N' number of magnetometers 26' may be given as:

$$\begin{bmatrix} \vec{B}_{TOT-MEAS}(x, y, z, t), 1 \\ \vec{B}_{TOT-MEAS}(x, y, z, t), 2 \\ \vdots \\ \vec{B}_{TOT-MEAS}(x, y, z, t), N' \end{bmatrix}. \quad [2]$$

As briefly discussed above, the processor 30 may determine the known actuated magnetic field $B_{ACT-KNOWN}$ at the magnetometers 26 based on a known profile of the set of magnetic field actuators 28 and the actuation strengths of the magnetic field actuators 28. In an exemplary embodiment, an M number of the magnetic field actuators 28 may apply an M×K actuations of the actuated magnetic field $B_{ACT}$ over time in accordance with the discretized matrix:

$$B_{ACT} = \begin{bmatrix} B_{ACT_{11}} & \cdots & B_{ACT_{1K}} \\ \vdots & \ddots & \vdots \\ B_{ACT_{M1}} & \cdots & B_{ACT_{MK}} \end{bmatrix}. \quad [3]$$

Assuming that the set of magnetic field actuators 28 comprises a triad of uniform magnetic field actuators 28a-28c (M=3) (as shown in FIG. 3) for respectively generating x-, y-, and z-components of the actuated magnetic field $B_{ACT}$ to cancel the outside magnetic field $B_{OUT}$ in all three dimensions, the actuated magnetic field $B_{ACT}$ can be defined as a vector $\vec{B}_{ACT}(x, y, z, t)$ that varies over space and time.

The set of magnetic field actuators 28 respectively have an M number of actuation strengths in the form of a vector $\vec{J}(t)$ (one for each magnetic field actuator 28) and a matrix of influence R by the actuation strength vector $\vec{J}(t)$ to the actuated magnetic field $\vec{B}_{ACT}(x, y, z, t)$ at an N number of magnetometers 26 (all of the magnetometers 26, i.e., the union of the N' number of first set of magnetometers 26' and an N" number of the second set of magnetometers 26"), as follows:

$$R = \begin{bmatrix} R_{11} & \cdots & R_{1M} \\ \vdots & \ddots & \vdots \\ R_{N1} & \cdots & R_{NM} \end{bmatrix}. \quad [4]$$

In the illustrated embodiment, the known profile of the actuated magnetic field $B_{ACT}$ may have, e.g., the trapezoidal shape illustrated in FIG. 5, and the matrix of influence R may be generated using mathematical or numerical modeling (e.g., by simulating the magnetic field emanating from each of the magnetic field actuators 28 to different spatial locations, e.g., at the N number of magnetometers 26) or by the performance of calibration measurements ahead of time (i.e., generate a nominal actuated magnetic field and measure the actuated magnetic field at different spatial locations, e.g., at the magnetometers 26) that quantifies the profile of the actuated magnetic field $B_{ACT}$ generated by each of magnetic field actuators 28, and therefore defines the influence of each magnetic field actuator 28 at the location of each magnetometer 26. The resulting actuated magnetic field at the locations of the magnetometers 26 will linearly scale with the actuation strength vectors $\vec{J}(t)$ of the magnetic field actuators 28, such that a known actuated magnetic field $\vec{B}_{ACT-KNOWN}(x, y, z, t)$ that varies over space and time at the N number of magnetometers 26 may be given as:

$$\begin{bmatrix} \vec{B}_{ACT-KNOWN}(x, y, z, t), 1 \\ \vec{B}_{ACT-KNOWN}(x, y, z, t), 2 \\ \vdots \\ \vec{B}_{ACT-KNOWN}(x, y, z, t), N \end{bmatrix} = [R]\vec{J}(t). \quad [5]$$

As briefly discussed above, the processor 30 may generate a generic model of the outside magnetic field $B_{OUT-MOD}$ in the vicinity of the magnetometers 26. In particular, on the length scale of the signal acquisition unit 18, the outside magnetic field $B_{OUT}$ may assume to have certain physical properties. The processor 30 may generate the generic outside magnetic field model $B_{OUT-MOD}$ in the vicinity of the magnetometers 26 based on these assumed physical properties in any one of a variety of manners, but in the illustrated embodiment, the processor 30 models the outside magnetic field $B_{OUT}$ as a function of space by employing one or more basis functions. In one embodiment, the processor 30 models the outside magnetic field $B_{OUT}$ by employing basis functions having a linear spatial dependence. For example, such basis functions may have uniform ($0^{th}$ order) components and linear (first order) spatial components (i.e., the slope), as illustrated in FIG. 5, although other selected basis functions can be used to model the outside magnetic field $B_{OUT}$. Second order non-linear spatial components can be ignored, although in alternative embodiments, basis functions with non-linear spatial dependence, or other types of modeling that one of ordinary skill in the art of signal processing, system identification, or control will recognize will serve the same purpose (such as other types of modes or bases, including singular values, eigenvectors, or bases collected from data such as collected by proper orthogonal decomposition or by other fitting methods).

Assuming that the outside magnetic field $B_{OUT}$ can be modeled with only $0^{th}$ order and $1^{st}$ order components, e.g., the linear gradient shape of the outside magnetic field $B_{OUT}$ illustrated in FIG. 5 (in one dimension), a time-varying and spatially-varying model of the outside magnetic field $\vec{B}_{OUT-MOD}(x, y, z, t)$ is:

$$\vec{B}_{OUT-MOD}(x, y, z, t) = \begin{bmatrix} Bx_{OUT-MOD}(x, y, z, t) \\ By_{OUT-MOD}(x, y, z, t) \\ Bz_{OUT-MOD}(x, y, z, t) \end{bmatrix} = \quad [6]$$

-continued $$\begin{bmatrix} \alpha_x(t) + \alpha_{xx}(t)x + \alpha_{xy}(t)y + \alpha_{xz}(t)z \\ \alpha_y(t) + \alpha_{yx}(t)x + \alpha_{yy}(t)y + \alpha_{yz}(t)z \\ \alpha_z(t) + \alpha_{zx}(t)x + \alpha_{zy}(t)y + \alpha_{zz}(t)z \end{bmatrix} + O(\|x, y, z\|^2),$$

Thus, the x-directional component $Bx_{OUT-MOD}(x, y, z, t)$ of the magnetic field model $\vec{B}_{OUT-MOD}(x, y, z, t)$ has a $0^{th}$ order component that is characterized by the time-varying basis function $\alpha_x(t)$ and $1^{st}$ order spatial components that linearly vary in the space (x, y, and z) and are respectively characterized by time varying basis functions $\alpha_{xx}(t)x$, $\alpha_{xy}(t)y$ and $\alpha_{xz}(t)z$; the y-directional component $By_{OUT-MOD}(x, y, z, t)$ of the magnetic field model $\vec{B}_{OUT-MOD}(x, y, z, t)$ has a $0^{th}$ order component that is characterized by the time-varying basis function $\alpha_y(t)$ and $1^{st}$ order spatial components that linearly vary in the space (x, y, and z) and are respectively characterized by time varying basis functions $\alpha_{yx}(t)x$, $\alpha_{yy}(t)y$, and $\alpha_{yz}(t)z$; and the y-directional component $Bz_{OUT-MOD}(x, y, z, t)$ of the magnetic field model $\vec{B}_{OUT-MOD}(x, y, z, t)$ has a $0^{th}$ order component that is characterized by the time-varying basis function $\alpha_z(t)$ and $1^{st}$ order spatial components that linearly vary in the space (x, y, and z) and are respectively characterized by time varying basis functions $\alpha_{zx}(t)x$, $\alpha_{zy}(t)y$, and $\alpha_{zz}(t)z$.

Thus, a total of 12 basis functions (i.e., $\alpha_x(t)$, $\alpha_{xx}(t)x$, $\alpha_{xy}(t)y$, $\alpha_{xz}(t)z$, $\alpha_y(t)$, $\alpha_{yx}(t)x$, $\alpha_{yy}(t)y$, $\alpha_{yz}(t)z$, $\alpha_z(t)$, $\alpha_{zx}(t)x$, $\alpha_{zy}(t)y$, $\alpha_{zz}(t)z$) characterizes the magnetic field model $\vec{B}_{OUT-MOD}(x, y, z, t)$. As will be described in further detail below, a coefficient vector $\vec{\gamma}(t)=[\gamma_1(t), \gamma_2(t), \ldots \gamma_{12}(t)]$ respectively associated with these basis functions can be estimated based on the total residual magnetic field measurements $\vec{B}_{TOT-MEAS}(x, y, z, t)$ acquired from the first set of magnetometers 26'. Higher order spatial components, such as second order terms in space like $x^2$, xy, and $z^2$, and third, fourth, and fifth order terms, etc., for this exemplary instance are assumed negligible.

In an optional technique, the processor 30 may constrain the outside magnetic field $\vec{B}_{OUT-MOD}(x, y, z, t)$ using Maxwell's equations, thereby decreasing the number of elements in the coefficient vector $\vec{\gamma}(t)$ to eight, as described in U.S. Provisional Application Ser. No. 62/975,723, entitled "Algorithms that Exploit Maxwell's Equations and Geometry to Reduce Noise for Ultra-Fine Measurements of Magnetic Fields from the Brain Using a Wearable MEG System", which is expressly incorporated herein by reference.

The generic outside magnetic field model $\vec{B}_{OUT-MOD}(x, y, z, t)$ at the magnetometers 26 can be represented by a matrix of influence Q from the coefficient vector $\vec{\gamma}(t)=[\gamma_1(t), \gamma_2(t), \ldots \gamma_{12}(t)]$ to the generic outside magnetic field model $\vec{B}_{OUT-MOD}(x, y, z, t)$ at the N number of magnetometers 26. Thus, the generic outside magnetic field model $\vec{B}_{OUT-MOD}(x, y, z, t)$ at the N number of magnetometers 26 may be given as:

$$\begin{bmatrix} \vec{B}_{OUT}(x, y, z, t), 1 \\ \vec{B}_{OUT}(x, y, z, t), 2 \\ \vdots \\ \vec{B}_{OUT}(x, y, z, t), N \end{bmatrix} = [Q]\vec{\gamma}(t). \quad [7]$$

One of ordinary skill in the art of signal processing, control, or optimization, will recognize that there are other possibilities for characterizing the outside magnetic field $\vec{B}_{OUT}(x, y, z, t)$ using a minimal (reduced number of coefficients) representation. For example, optimal or minimal modes may be selected based on intuition, on physical arguments, or on mathematical methods that aim to extract optimal modes (such as by proper orthogonal decomposition, singular value decomposition, eigenmode analysis, or by other optimization methods such as gradient descent, matrix methods, linear or non-linear programming, neural networks, genetic algorithms, or other optimization or analysis means).

As briefly discussed above, the processor 30 may parameterize the generic outside magnetic field model $\vec{B}_{OUT-MOD}(x, y, z, t)$ based on the total residual magnetic field $\vec{B}_{TOT-MEAS}(x, y, z, t)$ measured by the N' number of magnetometers 26' and the known actuated magnetic field $\vec{B}_{ACT-KNOWN}(x, y, z, t)$ at the N' number of magnetometers 26' to generate a parameterized outside magnetic field model $B_{OUT-PAR}$. The parameterized outside magnetic field model $B_{OUT-PAR}$ is generalized in that it can be applied to all of the magnetometers 26 (i.e., both the first set of magnetometers 26' and the second set of magnetometers 26").

In particular, assuming that the very weak MEG magnetic field $B_{MEG}$ can be ignored for purposes of simplicity, it is known that the following equation holds true at each of the magnetometers 26:

$$\begin{bmatrix} \vec{B}_{TOT}(x, y, z, t), 1 \\ \vec{B}_{TOT}(x, y, z, t), 2 \\ \vdots \\ \vec{B}_{TOT}(x, y, z, t), N' \end{bmatrix} = \begin{bmatrix} \vec{B}_{ACT}(x, y, z, t), 1 \\ \vec{B}_{ACT}(x, y, z, t), 2 \\ \vdots \\ \vec{B}_{ACT}(x, y, z, t), N' \end{bmatrix} + \begin{bmatrix} \vec{B}_{OUT}(x, y, z, t), 1 \\ \vec{B}_{OUT}(x, y, z, t), 2 \\ \vdots \\ \vec{B}_{OUT}(x, y, z, t), N' \end{bmatrix}, \quad [8]$$

where $\vec{B}_{TOT}(x, y, z, t)$ is the true total magnetic field measurement at the first set of magnetometers 26', $\vec{B}_{ACT}(x, y, z, t)$ is the true actuated magnetic field at the first set of magnetometers 26', and $\vec{B}_{OUT}(x, y, z, t)$ is the true outside magnetic field at the first set of first set of magnetometers 26'.

Substituting the total residual magnetic field measurements $\vec{B}_{TOT-MEAS}(x, y, z, t)$ at the first set of magnetometers 26' of the term [1] for the true total residual magnetic field $\vec{B}_{TOT}(x, y, z, t)$ at the first set of magnetometers 26' of equation [8], the known actuated magnetic field $\vec{B}_{ACT-KNOWN}(x, y, z, t)$ at the first set of magnetometers 26' of equation [5] for the true actuated magnetic field $\vec{B}_{ACT}(x, y, z, t)$ at the first set of magnetometers 26' of equation [8], and the generic outside magnetic field model $\vec{B}_{OUT-MOD}(x, y, z, t)$ at the magnetometers 26' of equation [5] for the true outside magnetic field $\vec{B}_{OUT}(x, y, z, t)$ at the first set of magnetometers 26' of equation [8] yields:

$$\begin{bmatrix} \overrightarrow{B_{TOT-MEAS}}(x,y,z,t),1 \\ \overrightarrow{B_{TOT-MEAS}}(x,y,z,t),2 \\ \vdots \\ \overrightarrow{B_{TOT-MEAS}}(x,y,z,t),N' \end{bmatrix} = [R]\vec{J}(t) + [Q]\vec{\gamma}(t) + \begin{bmatrix} \delta_1 \\ \delta_2 \\ \vdots \\ \delta_{N'} \end{bmatrix}, \quad [9]$$

where δ is unknown measurement noise for each magnetometer 26'.

The processor 30 may employ any suitable fitting optimization technique (including linear and nonlinear methods, gradient descent, matrix methods, system identification, or machine learning methods, etc.) to fit the coefficient vector (t) of the generic outside magnetic field model $\overrightarrow{B_{OUT-MOD}}$(x, y, z, t) to the difference between the total residual magnetic field $\overrightarrow{B_{TOT-MEAS}}$(x, y, z, t) measured by the first set of magnetometers 26' and the known actuated magnetic field $\overrightarrow{B_{ACT-KNOWN}}$(x, y, z, t) at the first set of magnetometers 26'. In the illustrated embodiment, the processor 30 employs a least squares or weighted least squares optimization technique, which serves to minimize the error between collected and known data and estimated data, to accurately estimate the values of the coefficient vectors (t) of the generic outside magnetic field model $\overrightarrow{B_{OUT-MOD}}$(x, y, z, t) at the first set of magnetometers 26'. That is, the solution that minimizes the difference between the total residual magnetic field $\overrightarrow{B_{TOT-MEAS}}$(x, y, z, t) measured by each of the magnetometers 26' and the product of the matrix of influence R at the magnetometers 26' and the vector of actuation strengths $\vec{J}(t)$ of the set of magnetic field actuators 28 yields an estimate of the coefficient vector $\vec{\gamma}^*(t)$ of the generic outside magnetic field model $\overrightarrow{B_{OUT-MOD}}$(x, y, z, t) at the magnetometers 26'.

Specifically, the least squares estimate of the coefficient vector $\vec{\gamma}^*(t)$ of the generic outside magnetic field model $\overrightarrow{B_{OUT-MOD}}$(x, y, z, t) can be provided as: $[14]\vec{\gamma}^*(t)=[Q^T Q]^{-1} Q^T (B_{TOT-MEAS}(t) - R * \vec{J}(t))$, where Q is the matrix of influence from the coefficient vector $\vec{J}(t)=[\gamma_1(t), \gamma_2(t), \ldots \gamma_8(t)]$ to the generic outside magnetic field model $\overrightarrow{B_{OUT-MOD}}$(x, y, z, t) at the N' number of magnetometers 26'; $B_{TOT-MEAS}(t)$ is the time-varying matrix of total residual magnetic field measurements $\overrightarrow{B_{TOT-MEAS}}$(x, y, z, t) at the N' number of magnetometers 26'; $\vec{J}(t)$ is the actuation strength vector; R is the matrix of influence from the actuation strength vector $\vec{J}(t)$ to the known actuated magnetic field $\overrightarrow{B_{ACT-KNOWN}}$(x, y, z, t) at the N' number of magnetometers 26'; the superscript T denotes the matrix transpose; and the superscript −1 denotes matrix inversion.

A parameterized outside magnetic field model $\overrightarrow{B_{OUT-PAR}}$(x, y, z, t) may be generated by substituting the solved coefficient vector $\vec{\gamma}^*(t)$ into equation [6]. It should be appreciated that the foregoing method transforms a discrete set of the total residual magnetic field measurements $\overrightarrow{B_{TOT-MEAS}}$(x, y, z, t) into continuous parameterizations of the outside magnetic field $\overrightarrow{B_{OUT}}$(x, y, z, t), i.e., the parameterized outside magnetic field model $\overrightarrow{B_{OUT-PAR}}$(x, y, z, t). This enables the processor 30 to estimate the outside magnetic field $B_{OUT}$ at arbitrary locations in the vicinity from which the measurements of the total residual magnetic field $B_{TOT-MEAS}$ were acquired, i.e., in the vicinity of the signal acquisition unit 18.

As briefly discussed above, the processor 30 may determine an outside magnetic field estimates $\overrightarrow{B_{OUT-EST}}$(x, y, z, t) at the second set of magnetometers 26" based on the parameterized outside magnetic field model $\overrightarrow{B_{OUT-PAR}}$(x, y, z, t). In particular, the outside magnetic field estimates $\overrightarrow{B_{OUT-EST}}$(x, y, z, t) at the second set of magnetometers 26" may be determined by substituting the (x,y,z) locations of the second set of magnetometers 26" into the parameterized outside magnetic field model $\overrightarrow{B_{OUT-PAR}}$(x, y, z, t); i.e., the outside magnetic field estimates $\overrightarrow{B_{OUT-EST}}$(x, y, z, t) at the second set of magnetometers 26" may be recovered from the product of the influence matrix Q and the least squares fit values of the coefficient vector $\vec{\gamma}^*(t)$.

As briefly discussed above, the processor 30 may determine the total residual magnetic field estimates $\overrightarrow{B_{TOT-EST}}$(x, y, z, t) at second set of magnetometers 26" based on the known actuated magnetic field $\overrightarrow{B_{ACT-KNOWN}}$(x, y, z, t) at the second set of magnetometers 26" and the outside magnetic field estimates $\overrightarrow{B_{OUT-EST}}$(x, y, z, t) at the second set of magnetometers 26". In particular, the processor 30 may sum the known actuated magnetic field $\overrightarrow{B_{ACT-KNOWN}}$(x, y, z, t) at the second set of magnetometers 26" and the outside magnetic field estimates $\overrightarrow{B_{OUT-EST}}$(x, y, z, t) at the second set of magnetometers 26".

In particular, substituting the total residual magnetic field estimates $\overrightarrow{B_{TOT-EST}}$(x, y, z, t) at the second set of magnetometers 26" for the true total residual magnetic field $\overrightarrow{B_{TOT}}$(x, y, z, t) at the second set of magnetometers 26" of equation [8], the known actuated magnetic field $\overrightarrow{B_{ACT-KNOWN}}$(x, y, z, t) at the second set of magnetometers 26" of equation [2] for the true actuated magnetic field $\overrightarrow{B_{ACT}}$(x, y, z, t) at the second set of magnetometers 26" of equation [8], and the outside magnetic field estimates $\overrightarrow{B_{OUT-EST}}$(x, y, z, t) at the second set of magnetometers 26" for the true outside magnetic field $\overrightarrow{B_{OUT}}$(x, y, z, t) at the second set of magnetometers 26" of equation [8] yields:

$$\begin{bmatrix} \overrightarrow{B_{TOT-EST}}(x,y,z,t),1 \\ \overrightarrow{B_{TOT-EST}}(x,y,z,t),2 \\ \vdots \\ \overrightarrow{B_{TOT-EST}}(x,y,z,t),N'' \end{bmatrix} = \quad [10]$$

$$\begin{bmatrix} \overrightarrow{B_{ACT-KNOWN}}(x,y,z,t),1 \\ \overrightarrow{B_{ACT-KNOWN}}(x,y,z,t),2 \\ \vdots \\ \overrightarrow{B_{ACT-KNOWN}}(x,y,z,t),N'' \end{bmatrix} + \begin{bmatrix} \overrightarrow{B_{OUT-EST}}(x,y,z,t),1 \\ \overrightarrow{B_{OUT-EST}}(x,y,z,t),2 \\ \vdots \\ \overrightarrow{B_{OUT-EST}}(x,y,z,t),N'' \end{bmatrix},$$

Thus, intuitively, equation [10] need only be solved to accurately infer the total residual magnetic field estimates $B_{TOT-EST}$ at the magnetometers 26.

It can be appreciated that inferring the estimated measurement $\vec{B}_{TOT\text{-}EST}(x, y, z, t)$ at the second set of magnetometers 26" based on the total residual magnetic field measurements $\vec{B}_{TOT\text{-}MEAS}(x, y, z, t)$ taken by the first set of magnetometers 26' (including magnetometers 26 that are also in the second set of magnetometers 26" for which the total residual magnetic field estimates $\vec{B}_{TOT\text{-}EST}(x, y, z, t)$ is being inferred) provides a more accurate assessment of the true total residual magnetic field $\vec{B}_{TOT}(x, y, z, t)$ at each magnetometer 26" than each magnetometer 26" can measure alone, because such inference technique averages out the unknown measurement noise δ of the magnetometers 26 in a rigorous manner. Thus, in effect, the total residual magnetic field measurement $\vec{B}_{TOT\text{-}MEAS}(x, y, z, t)$ taken by each magnetometer 26 is corrected by this inference technique.

Although all three of the directional components of the outside magnetic field $B_{OUT}$ and actuated magnetic field $B_{ACT}$, and thus all three of the directional components of the total residual magnetic field $B_{TOT}$, have been considered when inferring the total residual magnetic field estimates $B_{TOT\text{-}EST}$ at the second set of magnetometers 26", it should be appreciated that only one or two directional components of the outside magnetic field $B_{OUT}$ and/or actuated magnetic field $B_{ACT}$ may be considered when inferring the total residual magnetic field estimates $B_{TOT\text{-}EST}$ at the second set of magnetometers 26". Furthermore, although all three directional components of the total residual magnetic field $B_{TOT\text{-}MEAS}$ have been described as being measured at the same location or virtually at the same location for each magnetometer 26' and all three directional components of the total residual magnetic field $B_{TOT\text{-}EST}$ have been described as being estimated at the same location or virtually at the same location for each magnetometer 26", less than three directional components of the total residual magnetic field $B_{TOT\text{-}MEAS}$ may be measured at the same location or virtually at the same location for each magnetometer 26' and/or less than three directional components of the total residual magnetic field $B_{TOT\text{-}EST}$ may be estimated at the same location or virtually at the same location for each magnetometer 26.

As discussed above, the processor 30 may generate an outside magnetic field model $B_{OUT\text{-}MOD}$ by employing basis functions other than the linear basis functions, and in particular other functions than the uniform ($0^{th}$ order) spatial component and linear (first order) spatial component (i.e., the slope), as illustrated in FIG. 5. In one embodiment, set of mutually orthogonal vector fields with spatial patterns that are determined a-priori can be used as basis function. For example, complex-valued vector fields, known as the vector spherical harmonics (VSH), can be used to generate the basis modes for the outside magnetic field for $B_{OUT\text{-}MOD}$.

One of these families of functions is an infinite series of vector fields comprising a complete and orthogonal basis for magnetic field solutions to the quasi-static Maxwell equations with outside-head sources, the known mathematical properties of which have been derived in R. G. Barrera et al., "Vector Spherical Harmonics and Their Application to Magnetostatics," *Eur. J. Phys.*, Vol. 6, No. 4, pp. 287-294, October 1985. A combination of n VSH basis fields $w_i(r)$ can be expressed as follows:

$$B_{OUT\text{-}MOD}(r) = \sum_{i=0}^{n} \gamma_i w_i(r) + \epsilon(r), \qquad [12]$$

where r is the radius, $w_i$ is a basis function, n is the number of basis functions, i is the index for the basis function, $\epsilon(r)$ is the remaining error for the part of Maxwell's equations that are not captured by the first n modes, and $\gamma_i$ is a weighting coefficient in accordance with:

[13] $\gamma = W^{\dagger}\phi$, where $\phi$ is a vector of length equal to the number of magnetometers in the first set of magnetometers 26' and containing measurements of the outside magnetic field $B_{OUT}$ at the magnetometers 26', † denotes pseudoinverse, and n is the number of magnetometers in the first set of magnetometers 26', $\gamma_i$ is a weighting coefficient, and W is the matrix representing the basis function on the first set of magnetometers 26'. The matrix W has n vector columns of length equal to the number of magnetometers in the first set of magnetometers 26' and containing the dot products of the basis fields $w_i$ with the unit-length vectors describing the sensitive axes of the first set of magnetometers 26' at the location of the each of the magnetometers 26'. Because of these properties, a combination of n VSH basis fields $w_i(r)$ as set forth equation [12] is guaranteed to model the outside magnetic field $B_{OUT}$ at arbitrary locations r up to an error $\epsilon$ that decreases as the number independent measurements at the first set of magnetometers 26' increases.

Any optimization method, including linear and nonlinear methods, gradient descent, and machine learning methods, may be used to estimate the weighting coefficients $\gamma_i$ that multiply the basis functions to represent the outside magnetic field at each moment, and thus generate the parameterized outside magnetic field model $B_{OUT\text{-}PAR}$ (representative of the actual outside magnetic field $B_{OUT}$ in the vicinity of the magnetometers 26), which can then be used to estimate the generic outside magnetic field model $B_{OUT\text{-}EST}$ at the second set of magnetometers 26", as discussed above with respect to equation [8], which can then be solved to accurately estimate the total residual magnetic field $B_{TOT\text{-}EST}$ at the second set of magnetometers 26."

This same process of fitting weighting coefficients may be applied to models using other basis vector fields, such as vector fields comprising sums of sines and cosines or Taylor's series expansions in polynomials. Other classes of continuous parametrizations may use sets of basis vector fields that are not mutually orthogonal or that do not span the full space of solutions to Maxwell's equations.

Figure 7:
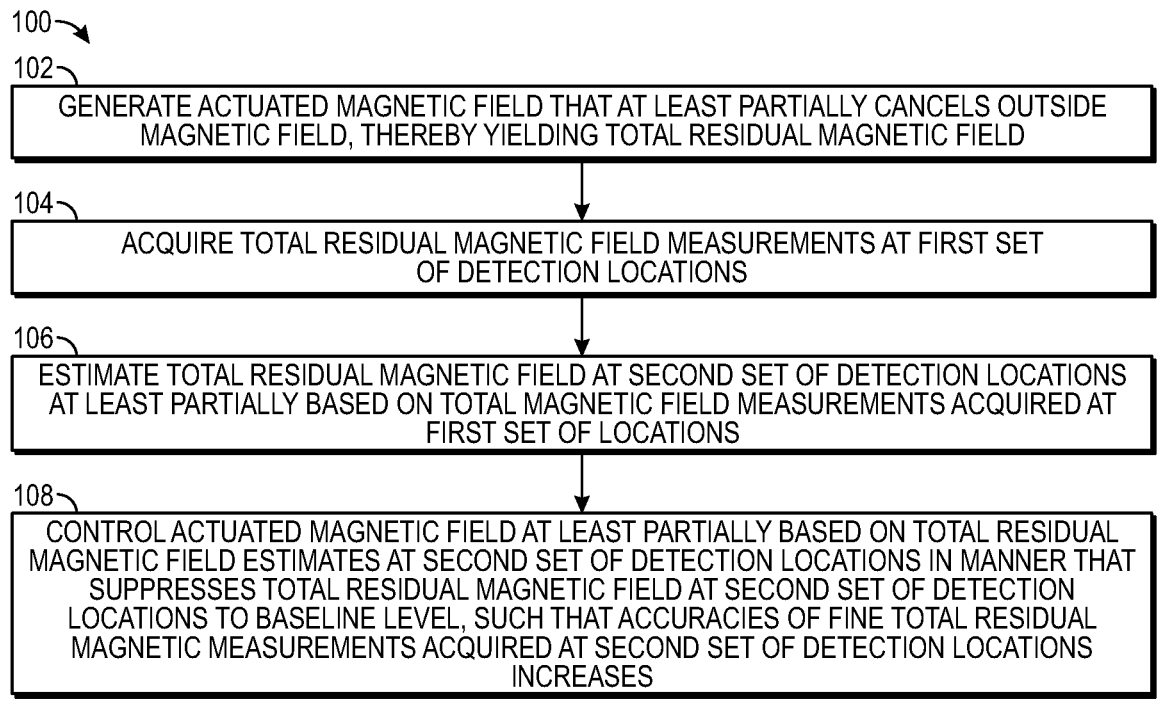
FIG. 7 is a flow diagram illustrating one exemplary generic method of operating the signal acquisition unit of FIG. 4.

Referring now to FIG. 7, one exemplary method 100 of suppressing a total residual magnetic field $B_{OUT}$ will be described.

The method 100 comprises generating the actuated magnetic field $B_{ACT}$ that at least partially cancels an outside magnetic field $B_{OUT}$ (e.g., via the set of magnetic field actuators 28 of the signal processing unit 20), thereby yielding a total residual magnetic field $B_{TOT}$ (step 102). In the preferred embodiment, the actuated magnetic field $B_{ACT}$ is generated in all three dimensions and is uniform, although in alternative embodiments, the actuated magnetic field $B_{ACT}$ may be generated in less three dimensions and may be non-uniform (e.g., a gradient).

The method 100 further comprises acquiring the total residual magnetic field measurements $B_{TOT\text{-}MEAS}$ respectively at a first set of a plurality of detection locations (e.g., from the coarse magnetometers 26a and/or fine magnetometers 26b of the signal acquisition unit 20) (step 104), and estimating the total residual magnetic field $B_{TOT\text{-}EST}$ at a second set of a plurality of detection locations (e.g., from the coarse magnetometers 26a and/or fine magnetometers 26b of the signal acquisition unit 20) based on the total residual magnetic field measurements $B_{TOT\text{-}MEAS}$ acquired at the first set of detection locations (step 106). The first set of detection locations and the second set of detection locations may have no common detection location (meaning that there is no detection location where a total residual magnetic field is both measured and estimated, e.g., no magnetometer 26 in common), may have at least one common detection location (meaning that there is at least one detection location where the total residual magnetic field is both measured and estimated, e.g., at least one magnetometer 26 in common), or all of the first set of detection locations and all of the second set of detection locations may be common (meaning that total residual magnetic field is both measured and estimated at all of the detection locations, e.g., all magnetometers 26 are common).

The method 100 further comprises controlling the actuated magnetic field $B_{ACT}$ at least partially based on the total residual magnetic field estimates $B_{TOT-EST}$ at the second set of detection locations in a manner that suppresses the total residual magnetic field $B_{TOT}$ at the second set of locations to a baseline level (by cancelling the outside magnetic field $B_{OUT}$, e.g., via the coarse feedback control loop 50 and/or fine feedback control loop 52 and sending noise-cancelling control signals C to the set of magnetic field actuators 28 of the signal acquisition unit 18), such that accuracies of the total residual magnetic field measurements $B_{TOT-MEAS}$ acquired at the second set of locations increase (e.g., the fine magnetometers 26b of the signal acquisition unit 20 come in-range) (step 108).

The method 100 may be applied to a first set of detection locations where coarse total residual magnetic field measurements $B_{TOT-MEAS}$ are taken and to a second set of detection locations where fine total residual magnetic field measurements $B_{TOT-MEAS}$ are taken.

Figure 8:
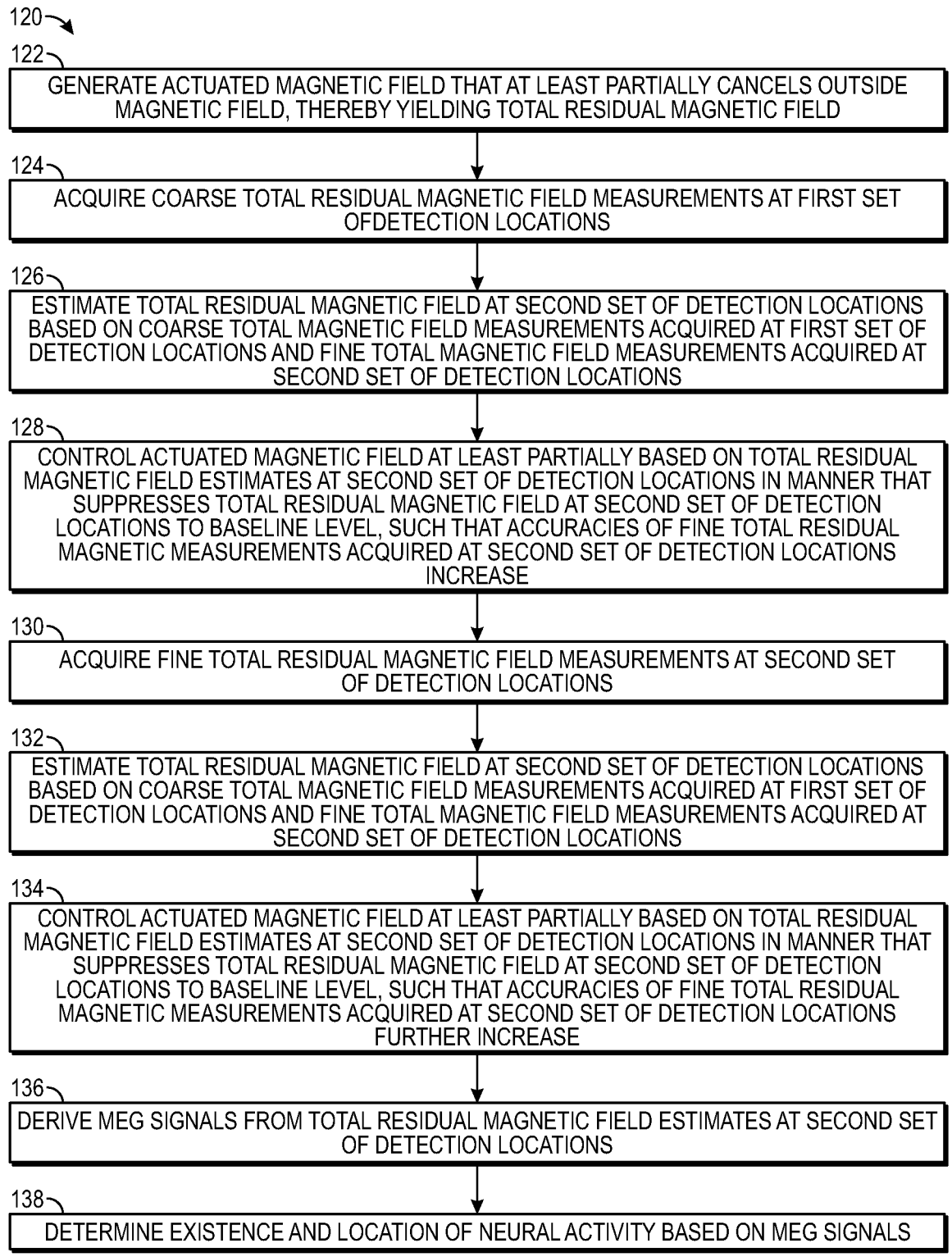
FIG. 8 is a flow diagram illustrating one exemplary specific method of operating the signal acquisition unit of FIG. 4 in accordance with the generic method of FIG. 7.

For example, referring to FIG. 8, one particular method 120 comprises generating the actuated magnetic field $B_{ACT}$ that at least partially cancels an outside magnetic field $B_{OUT}$ (e.g., via the set of magnetic field actuators 28 of the signal processing unit 20), thereby yielding a total residual magnetic field $B_{TOT}$ (step 122). The method 120 further comprises acquiring coarse total residual magnetic field measurements $B_{TOT-MEAS}$ at the first set of detection locations (e.g., from the coarse magnetometers 26a of the signal acquisition unit 20) (step 124). The method 120 further comprises estimating the total residual magnetic field $B_{TOT-EST}$ at the second set of detection locations (e.g., at the fine magnetometers 26b of the signal acquisition unit 20) based on the coarse total residual magnetic field measurements $B_{TOT-MEAS}$ acquired at the first set of detection locations (step 126).

The method 120 further comprises controlling the actuated magnetic field $B_{ACT}$ at least partially based on the total residual magnetic field estimates $B_{TOT-EST}$ at the second set of detection locations in a manner that at least partially cancels the outside magnetic field $B_{OUT}$ at the second set of detection locations (e.g., via the coarse feedback control loop 50 and sending noise-cancelling control signals C to the set of magnetic field actuators 28 of the signal acquisition unit 20), thereby suppressing the total residual magnetic field $B_{TOT}$ at the second set of detection locations (e.g., at the fine magnetometers 26b of the signal acquisition unit 20) to a baseline level, such that accuracies of the fine total residual magnetic field measurements $B_{TOT-MEAS}$ acquired at the second set of detection locations increase (e.g., the fine magnetometers 26b of the signal acquisition unit 20 come in-range) (step 128).

The method 120 further comprises acquiring the fine total residual magnetic field measurements at the second set of detection locations (e.g., from the fine magnetometers 26b of the signal acquisition unit 20) (step 130), estimating the total residual magnetic field $B_{TOT-EST}$ at the second set of detection locations (e.g., at the fine magnetometers 26b of the signal acquisition unit 20) based on the coarse total residual magnetic field measurements $B_{TOT-MEAS}$ acquired at the second set of detection locations (step 132), and controlling the actuated magnetic field $B_{ACT}$ at least partially based on the total residual magnetic field estimates $B_{TOT-EST}$ at the second set of detection locations in a manner that further suppresses the total residual magnetic field at the second set of detection locations to a lower level (by further cancelling the outside magnetic field $B_{OUT}$, e.g., via the fine feedback control loop 52 and sending noise-cancelling control signals C to the set of magnetic field actuators 28 of the signal acquisition unit 18) (step 134).

The method further comprises deriving a plurality of MEG signals $S_{MEG}$ respectively from the total residual magnetic field estimates $B_{TOT-EST}$ at the second set of detection locations (e.g., via the signal acquisition unit 18) (step 136). That is, because the total residual magnetic field measurements $B_{TOT-MEAS}$ respectively at the first set of detection locations total residual magnetic field $B_{TOT}$ contains the MEG magnetic field $B_{MEG}$ from the brain 14 of the user 12, and thus by inference, the total residual magnetic field estimates $B_{TOT-EST}$ at the second set of detection locations contains the MEG magnetic field $B_{MEG}$ from the brain 14 of the user 12, the MEG signals $S_{MEG}$ can be extracted from the total residual magnetic field estimates $B_{TOT-EST}$. The existence and detection location of neural activity in the brain 14 of the user 12 may then be determined based on the MEG signals $S_{MEG}$ (e.g., via the signal processing unit 20) (step 138).

Figure 9:
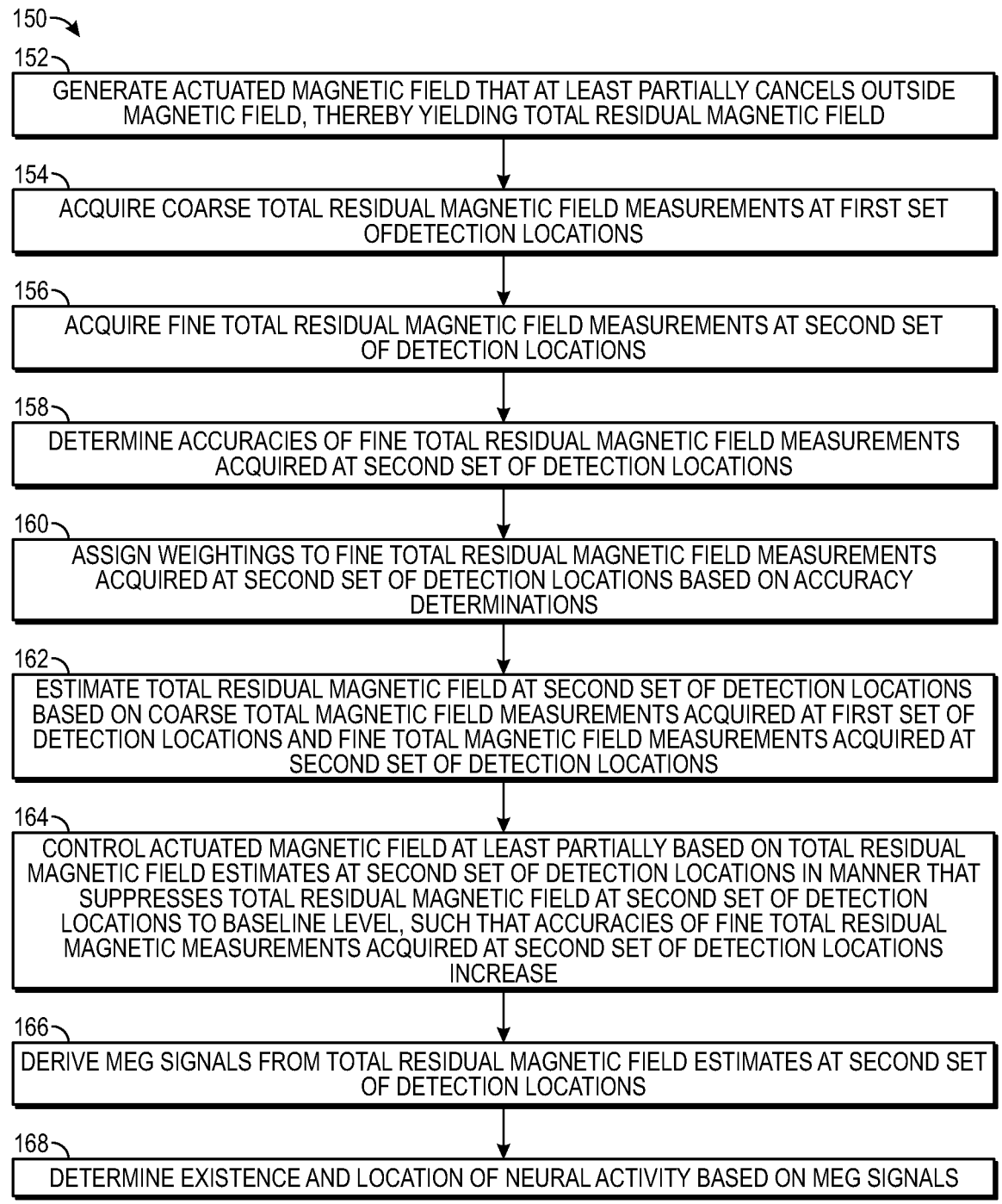
FIG. 9 is a flow diagram illustrating another exemplary specific method of operating the signal acquisition unit of FIG. 4 in accordance with the generic method of FIG. 7.

As another example, referring to FIG. 9, another particular method 150 comprises generating the actuated magnetic field $B_{ACT}$ that at least partially cancels an outside magnetic field $B_{OUT}$, (e.g., via the set of magnetic field actuators 28 of the signal processing unit 20), thereby yielding a total residual magnetic field $B_{TOT}$ (step 152). The method 120 further comprises acquiring measurements of the total residual magnetic field $B_{TOT}$ at a plurality of detection locations. In particular, the method 150 comprises acquiring coarse total residual magnetic field measurements $B_{TOT-MEAS}$ at the first set of detection locations (e.g., from the coarse magnetometers 26a of the signal acquisition unit 20) (step 154), and acquiring fine total residual magnetic field measurements $B_{TOT-MEAS}$ at the second set of detection locations (e.g., from the fine magnetometers 26b of the signal acquisition unit 20) (step 156).

The method 150 further comprises determining accuracies of the fine total residual magnetic field measurements $B_{TOT-MEAS}$ acquired at the second set of detection locations (e.g., by determining whether the fine magnetometers 26b of the signal acquisition unit 20 are in-range) (step 158), and assigning weightings to the fine total residual magnetic field measurements $B_{TOT-MEAS}$ acquired at the second set of detection locations (e.g., by assigning weightings to the fine magnetometers 26b of the signal acquisition unit 20) based on the accuracy determination (step 160). The method 150 further comprises estimating the total residual magnetic field $B_{TOT-EST}$ at the second set of detection locations (e.g., at the fine magnetometers 26b of the signal acquisition unit 20) based on the coarse total residual magnetic field measurements $B_{TOT-MEAS}$ acquired at the first set of detection locations and total residual magnetic field measurements $B_{TOT-MEAS}$ acquired at the first set of detection locations (step 162).

The method 120 further comprises controlling the actuated magnetic field $B_{ACT}$ at least partially based on the total residual magnetic field estimates $B_{TOT-EST}$ at the second set of detection locations in a manner that suppresses the total residual magnetic field $B_{TOT}$ at the second set of detection locations to a baseline level (by cancelling the outside magnetic field $B_{OUT}$, e.g., via the coarse feedback control loop 50 and/or fine feedback control loop 52 and sending noise-cancelling control signals C to the set of magnetic field actuators 28 of the signal acquisition unit 18), such that accuracies of the fine total residual magnetic field measurements $B_{TOT-MEAS}$ acquired at the second set of detection locations increase (step 164).

The method further comprises deriving a plurality of MEG signals $S_{MEG}$ respectively from the total residual magnetic field estimates $B_{TOT-EST}$ at the second set of detection locations (e.g., via the signal acquisition unit 18) (step 166). The existence and detection location of neural activity in the brain 14 of the user 12 may then be determined based on the MEG signals $S_{MEG}$ (e.g., via the signal processing unit 20) (step 168).

Figure 10:
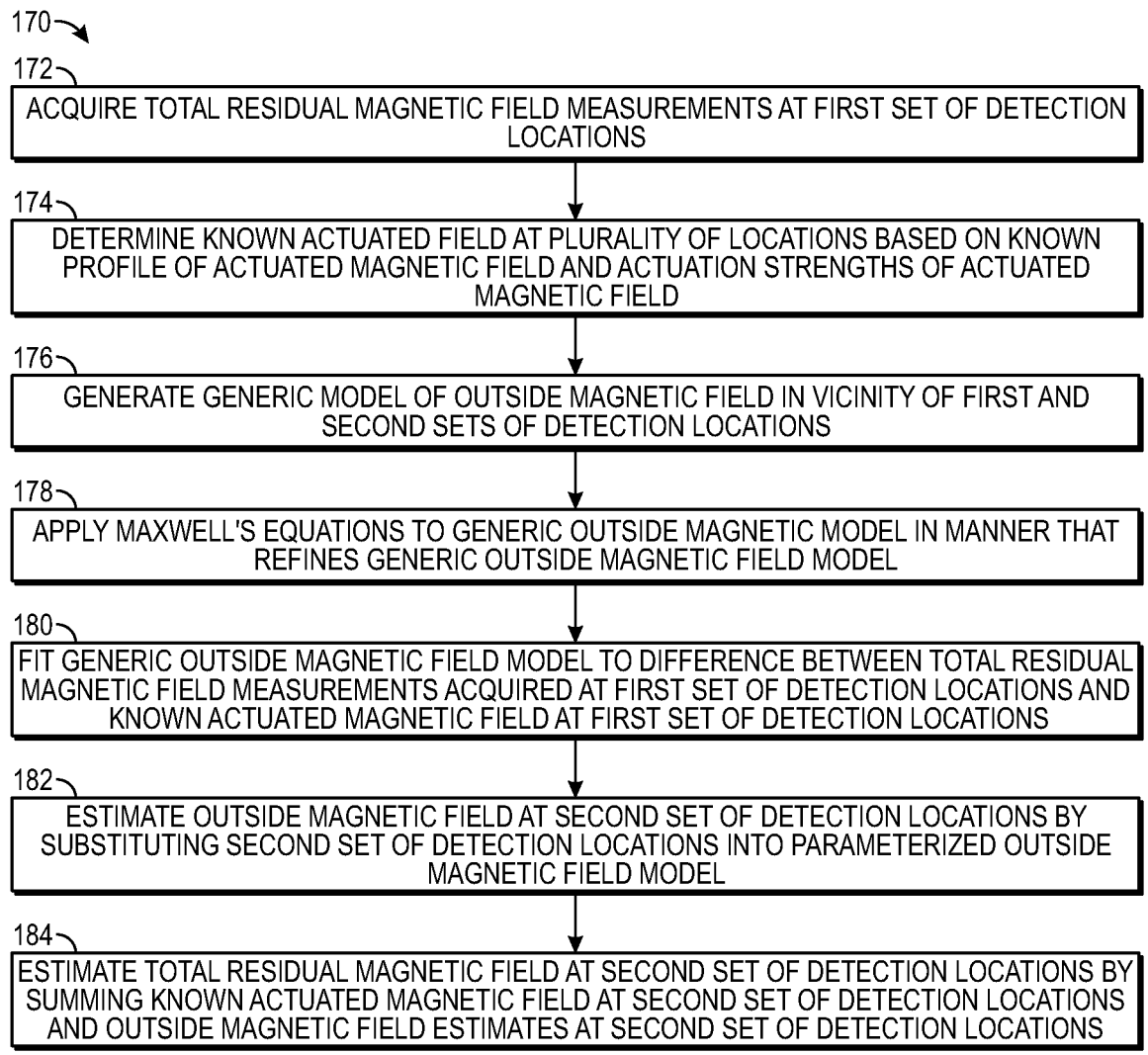
FIG. 10 is a flow diagram illustrating one exemplary method of estimating a total residual magnetic field in accordance with the generic method of FIG. 7.

Referring now to FIG. 10, one exemplary method 170 of estimating the total residual magnetic field $B_{TOT-EST}$ at the second set of detection locations (e.g., from the coarse magnetometers 26a and/or fine magnetometers 26b of the signal acquisition unit 18) comprises acquiring the total residual magnetic field measurements $B_{TOT-MEAS}$ at the first set of the detection locations (e.g., from the coarse magnetometers 26a and/or fine magnetometers 26b of the signal acquisition unit 18) (step 172). The method 170 further comprises determining a known actuated magnetic field $B_{ACT-KNOWN}$ at the first set of detection locations and the second set of detection locations based on a known profile of the actuated magnetic field actuated magnetic field $B_{ACT}$ and actuation strengths of the actuated magnetic field $B_{ACT}$ (step 174).

The method 170 further comprises generating a parameterized model of the outside magnetic field $B_{MOD-PAR}$ in the vicinity of the first set of detection locations and second set of detection locations based on the total residual magnetic field measurements $B_{TOT-MEAS}$ acquired at the first set of detection locations and the known actuated magnetic field $B_{ACT-KNOWN}$ at the first set of detection locations.

In the illustrated embodiment, the parameterized model of the outside magnetic field $B_{MOD-PAR}$ is generated by first generating a generic model of the outside magnetic field $B_{ACT-MOD}$ comprising a plurality of basis functions in the vicinity of the plurality of detection locations (step 176), optionally applying Maxwell's equations to the generic outside magnetic field model $B_{ACT-MOD}$ in a manner that constrains generic outside magnetic field model $B_{ACT-MOD}$ by reducing the number of the basis functions (step 178). In one embodiment, the basis functions comprise $0^{th}$ order basis functions and 1st order basis functions. In another embodiment, the basis functions comprise at least one non-linear basis function (e.g., a vector spherical harmonics (VSH) basis function).

The generic outside magnetic field $B_{ACT-MOD}$ is then parameterized based on the total residual magnetic field measurements $B_{TOT-MEAS}$ acquired at the first set of detection locations and the known actuated magnetic field $B_{ACT-KNOWN}$ at the first set of detection locations, thereby yielding a parameterized outside magnetic field model $B_{MOD-PAR}$ In particular, the generic outside magnetic field model $B_{ACT-MOD}$ (constrained or unconstrained) is fitted to a difference between the total residual magnetic field measurements $B_{TOT-MEAS}$ acquired at the first set of detection locations and the known actuated magnetic field $B_{ACT-KNOWN}$ at the first set of detection locations (step 180). For example, fitting the generic outside magnetic field model $B_{ACT-MOD}$ may comprises fitting coefficients of the plurality of basis functions to the difference between the total residual magnetic field measurements $B_{TOT-MEAS}$ acquired at the first set of detection locations and the known actuated magnetic field $B_{ACT-KNOWN}$ at the first set of detection locations, e.g., using a least squares optimization technique. The fitted coefficients may then be incorporated into the generic outside magnetic field model $B_{ACT-MOD}$, thereby yielding the parameterized outside magnetic field model $B_{MOD-PAR}$.

The method 170 further comprises estimating the outside magnetic field $B_{OUT-EST}$ at the second set of detection locations based on the parameterized outside magnetic field model $B_{MOD-PAR}$, and in particular, by substituting second set of detection locations into the parameterized outside magnetic field model $B_{MOD-PAR}$ (step 182). Lastly, the method 170 comprises estimating the total residual magnetic field $B_{TOT-EST}$ at the second set of detection locations based on the known actuated magnetic field $B_{ACT-KNOWN}$ at the second set of detection locations and the outside magnetic field estimates $B_{OUT-EST}$ at the second set of detection locations, and in particular, by summing the known actuated magnetic field $B_{ACT-KNOWN}$ at the second set of detection locations and the outside magnetic field estimates $B_{OUT-EST}$ at the second set of detection locations (step 184).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:
1. A system, comprising:
at least one magnetic field actuator configured for generating an actuated magnetic field that at least partially cancels an outside magnetic field, thereby yielding a total residual magnetic field;
a plurality of magnetometers including a plurality of coarse magnetometers and a plurality of fine magnetometers, the plurality of coarse magnetometers configured for taking coarse measurements of the total residual magnetic field respectively at the plurality of coarse magnetometers while the total residual magnetic field at the plurality of fine magnetometers is outside operating ranges of the plurality of fine magnetometers; and
a processor configured for acquiring the coarse total residual magnetic field measurements from the plurality of coarse magnetometers, determining estimates of the total residual magnetic field at the plurality of fine magnetometers based on the coarse total residual magnetic field measurements acquired from the plurality of coarse magnetometers, the determined estimates of the total residual magnetic field being different from the acquired coarse total residual magnetic field measurements, and controlling the actuated magnetic field at least partially based on the total residual magnetic field estimates at the plurality of fine magnetometers in a manner that suppresses the total residual magnetic field at the plurality of fine magnetometers to baseline levels that within operating ranges of the plurality of fine magnetometers.

2. The system of claim 1, further comprising:
a signal acquisition unit configured for being worn on a head of a user, the signal acquisition unit comprising a support structure, the at least one magnetic field actuator affixed to the support structure, the plurality of magnetometers affixed to the support structure, the signal acquisition unit configured for deriving a plurality of magnetoencephalography (MEG) signals respectively from the total residual magnetic field estimates at the plurality of fine magnetometers; and
a signal processing unit configured for determining an existence of neural activity in the brain of the user based on the plurality of MEG signals.

3. The system of claim 1, wherein the at least one magnetic field actuator comprises three orthogonal magnetic field actuators.

4. The system of claim 1, wherein each of the at least one magnetic field actuator comprises a uniform magnetic field actuator.

5. The system of claim 1, wherein each of the plurality of coarse magnetometers is a flux gate magnetometer, and each of the plurality of fine magnetometers is an optically pumped magnetometer (OPM).

6. The system of claim 1, wherein the plurality of fine magnetometers are configured for taking fine measurements of the total residual magnetic field respectively at the plurality of fine magnetometers after the plurality of fine magnetometers are in-range, and wherein the processor is configured for acquiring the fine total residual magnetic field measurements respectively from the plurality of fine magnetometers and controlling the actuated magnetic field at least partially based on the fine total residual magnetic field measurements acquired from the plurality of fine magnetometers in a manner that further suppresses the total residual magnetic field at the plurality of fine magnetometers to a lower level.

7. The system of claim 1, wherein the plurality of magnetometers further includes at least one other fine magnetometer different from the plurality of fine magnetometers, wherein the at least one other fine magnetometer is configured for taking fine measurements of the total residual magnetic field respectively at the at least one other fine magnetometer while the total residual magnetic field at the plurality of fine magnetometers is outside operating ranges of the plurality of fine magnetometers, and wherein the processor is configured for determining whether each of the at least one other fine magnetometer is in-range or out-of-range, and assigning a weighting to the each fine magnetometer based on the in-range or out-of-range determination, and wherein the processor is further configured for acquiring the fine total residual magnetic field measurements from the at least one other fine magnetometer, and controlling the actuated magnetic field further based on the fine total residual magnetic field measurements acquired from the at least one other fine magnetometer in a manner that suppresses the total residual magnetic field at the plurality of fine magnetometers to the baseline levels within the operating ranges of the plurality of fine magnetometers.

8. The system of claim 1, wherein the processor is configured for determining the estimates of the total residual magnetic field at the plurality of fine magnetometers by determining a known actuated magnetic field at the plurality of magnetometers, generating a parameterized model of the outside magnetic field in the vicinity of the plurality of magnetometers based on the total residual magnetic field measurements acquired from the plurality of coarse magnetometers and the known actuated magnetic field at the plurality of coarse magnetometers, estimating the outside magnetic field at the plurality of fine magnetometers based on the parameterized outside magnetic field model, and determining the estimates of the total residual magnetic field at the plurality of fine magnetometers based on the known actuated magnetic field at the plurality of fine magnetometers and the outside magnetic field estimates at the plurality of fine magnetometers.

9. The system of claim 1, wherein the plurality of fine magnetometers are out-of-range prior to suppressing the total residual magnetic field at the plurality of fine magnetometers to the baseline levels within the operating ranges of the plurality of fine magnetometers.

10. The system of claim 1, wherein each of the plurality of magnetometers is configured for taking measurements of the total residual magnetic field in three dimensions.

11. The system of claim 1, wherein the plurality of coarse magnetometers is respectively at a plurality of first locations, and the plurality of fine magnetometers is respectively at a plurality of second locations different from the plurality of first locations.

12. The system of claim 7, wherein determining whether each of the at least one other fine magnetometer is in-range or out-of-range comprises determining whether the each fine magnetometer is in a linear operating range, non-linear operating range, or saturated, and the weighting is assigned to the each fine magnetometer based on the linear operating range, non-linear operating range, or saturated determination.

13. The system of claim 12, wherein the processor is configured for assigning a full weighting to each of the at least one other fine magnetometer that are determined to be in the linear operating range, no weighting to each of the at least one other fine magnetometer that are determined to be saturated, and a partial weighting to each of the at least one other fine magnetometer that are determined to be in the non-linear operating range.

14. The system of claim 8, wherein the processor is configured for determining the known actuated magnetic field at the plurality of magnetometers based on a known profile of the at least one magnetic field actuator and at least one actuation strength respectively of the at least one magnetic field actuator.

15. The system of claim 8, wherein the processor is configured for determining the estimates of the total residual magnetic field at the plurality of fine magnetometers by summing the known actuated magnetic field at the plurality of fine magnetometers and the outside magnetic field estimates at the plurality of fine magnetometers.

16. The system of claim 8, wherein the processor is configured for determining the estimates of the outside magnetic field at the plurality of fine magnetometers by substituting locations of the plurality of fine magnetometers into the parameterized outside magnetic field model.

17. The system of claim 8, wherein the parameterized outside magnetic field model is configured for allowing the outside magnetic field to be estimated at arbitrary locations in the vicinity of the fine magnetometers.

18. The system of claim 16, wherein the processor is configured for generating the parameterized outside magnetic field model by generating a generic model of the outside magnetic field in the vicinity of the plurality of magnetometers, and parameterizing the generic outside magnetic field model based on the coarse total residual magnetic fields acquired from the plurality of coarse magnetometers and the known actuated magnetic field at the plurality of coarse magnetometers.

19. The system of claim 18, wherein the processor is configured for parameterizing the generic outside magnetic field model by fitting the generic outside magnetic field model to a difference between the coarse total residual magnetic fields acquired from the plurality of coarse magnetometers and the known actuated magnetic field at the plurality of coarse magnetometers.

20. The system of claim 19, wherein the generic outside magnetic field model comprises a plurality of basis functions, wherein the processor is configured for fitting the generic outside magnetic field model by fitting coefficients of the plurality of basis functions to the difference between the coarse total residual magnetic fields acquired from the plurality of coarse magnetometers and the known actuated magnetic field at the plurality of coarse magnetometers.

21. The system of claim 20, wherein the processor is configured for fitting the coefficients of the plurality of basis functions to the difference between the coarse total residual magnetic fields acquired from the plurality of coarse magnetometers and the known actuated magnetic field at the plurality of coarse magnetometers using a least squares optimization technique.

22. The system of claim 20, wherein the plurality of basis functions comprises $0^{th}$ order basis functions and 1st order basis functions.

23. The system of claim 20, wherein the processor is configured for applying Maxwell's equations to the generic outside magnetic field model in a manner that reduces the number of the plurality of basis functions.

24. The system of claim 21, wherein the processor is configured for generating the parameterized outside magnetic field model by incorporating the fitted coefficients into the generic outside magnetic field model.

25. The system of claim 24, wherein the plurality of basis functions comprises at least one non-linear basis function.

26. The system of claim 25, wherein the at least one non-linear basis function comprises a vector spherical harmonics (VSH) basis function.

27. The system of claim 9, wherein the processor is configured for acquiring and ignoring total residual magnetic field measurements respectively from the plurality of out-of-range fine magnetometers when controlling the actuated magnetic field in a manner that suppresses the total residual magnetic field at the plurality of fine magnetometers to the baseline levels within the operating ranges of the plurality of fine magnetometers.

* * * * *